US012678635B2

(12) United States Patent　　　(10) Patent No.:　US 12,678,635 B2
Zhou et al.　　　　　　　　　　　(45) Date of Patent:　　Jul. 14, 2026

(54) SYSTEMS AND METHODS FOR RADIOTHERAPY PLANNING

(71) Applicant: SHANGHAI UNITED IMAGING HEALTHCARE CO., LTD., Shanghai (CN)

(72) Inventors: Jingjie Zhou, Shanghai (CN); Supratik Bose, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1004 days.

(21) Appl. No.: 17/819,640

(22) Filed: Aug. 15, 2022

(65) Prior Publication Data

US 2022/0387822 A1　　Dec. 8, 2022

Related U.S. Application Data

(63) Continuation of application No. PCT/CN2020/098734, filed on Jun. 29, 2020.

(51) Int. Cl.
*A61N 5/10*　　　　(2006.01)

(52) U.S. Cl.
CPC ........... *A61N 5/1031* (2013.01); *A61N 5/103* (2013.01); *A61N 5/1039* (2013.01);
(Continued)

(58) Field of Classification Search
CPC ........ A61N 5/10; A61N 5/103; A61N 5/1031; A61N 5/1039; A61N 5/1042; A61N 5/1045; A61N 5/1047; A61N 5/1048;

A61N 5/1049; A61N 2005/1052; A61N 2005/1055; A61N 2005/1061; A61N 5/1064; A61N 5/1065; A61N 5/1067;
(Continued)

(56) References Cited

U.S. PATENT DOCUMENTS 8,363,784 B2 * 1/2013 Sobering .............. A61N 5/1031
　　　　　　　　　　　　　　　　　378/65
10,188,873 B2 * 1/2019 Kuusela ............... A61N 5/1031
(Continued)

FOREIGN PATENT DOCUMENTS

CN　　　107469239 A　　12/2017
CN　　　111001097 A　　4/2020
(Continued)

OTHER PUBLICATIONS

International Search Report in PCT/CN2020/098734 mailed on Mar. 25, 2021, 4 pages.
(Continued)

*Primary Examiner* — Allen C. Ho
(74) *Attorney, Agent, or Firm* — Metis IP LLC

(57)　　　　ABSTRACT

The present disclosure may provide a system for radiotherapy planning. The system may obtain planning information relating to at least one beam to be delivered to a subject in a treatment of the subject. The system may also generate an input of a fluence map generation model based on the planning information. For each of the at least one beam, the system may further generate at least one deliverable fluence map relating to at least one segment of the beam based on the input and the fluence map generation model.

20 Claims, 11 Drawing Sheets

500

(52) U.S. Cl.
CPC ......... *A61N 5/1045* (2013.01); *A61N 5/1047* (2013.01); *A61N 2005/1074* (2013.01); *A61N 2005/1089* (2013.01)

(58) Field of Classification Search
CPC .... A61N 2005/1074; A61N 2005/1087; A61N 2005/1089
USPC ......................................................... 378/65
See application file for complete search history.

(56) References Cited

U.S. PATENT DOCUMENTS

| | | | | |
|---|---|---|---|---|
| 10,507,337 | B2 * | 12/2019 | Willcut | A61N 5/1038 |
| 10,688,320 | B2 * | 6/2020 | Voronenko | A61N 5/1045 |
| 10,744,343 | B2 * | 8/2020 | Sjölund | A61N 5/1031 |
| 10,751,548 | B2 * | 8/2020 | Han | A61N 5/1039 |
| 10,796,793 | B2 * | 10/2020 | Zankowski | A61N 5/1039 |
| 10,867,417 | B2 * | 12/2020 | Han | A61N 5/1039 |
| 11,011,264 | B2 * | 5/2021 | Zankowski | A61N 5/1039 |
| 11,065,471 | B2 * | 7/2021 | Wu | A61N 5/103 |
| 11,071,877 | B2 * | 7/2021 | Zhou | A61N 5/1031 |
| 11,077,320 | B1 * | 8/2021 | Hibbard | A61N 5/1031 |
| 11,097,128 | B2 * | 8/2021 | Sjölund | A61N 5/1031 |
| 11,167,152 | B2 * | 11/2021 | Liu | A61N 5/103 |
| 11,367,520 | B2 * | 6/2022 | Sjölund | A61N 5/1031 |
| 11,383,104 | B2 * | 7/2022 | Maltz | A61N 5/103 |
| 11,491,350 | B2 * | 11/2022 | Lou | A61N 5/103 |
| 11,557,390 | B2 * | 1/2023 | Hibbard | A61N 5/1031 |
| 11,605,452 | B2 * | 3/2023 | Adler | A61N 5/1031 |
| 11,756,160 | B2 * | 9/2023 | Park | A61N 5/1049 382/276 |
| 11,756,667 | B2 * | 9/2023 | Lou | A61N 5/103 600/408 |
| 11,759,660 | B2 * | 9/2023 | Han | A61N 5/103 600/1 |
| 11,813,479 | B2 * | 11/2023 | Czeizler | A61N 5/1031 |
| 11,850,445 | B2 * | 12/2023 | Hibbard | A61N 5/1031 |
| 11,969,283 | B2 * | 4/2024 | Siversson | A61N 5/1039 |
| 12,005,270 | B2 * | 6/2024 | Li | A61N 5/1031 |
| 2018/0272152 | A1 | 9/2018 | Kuusela et al. | |
| 2018/0311509 | A1 | 11/2018 | Sjölund et al. | |
| 2019/0051398 | A1 | 2/2019 | Zankowski et al. | |
| 2019/0076671 | A1 | 3/2019 | Willcut et al. | |
| 2019/0192880 | A1 | 6/2019 | Hibbard | |
| 2019/0336793 | A1 | 11/2019 | Zhou et al. | |
| 2021/0187326 | A1 | 6/2021 | Han et al. | |

FOREIGN PATENT DOCUMENTS

| | | |
|---|---|---|
| WO | 2019160958 A1 | 8/2019 |
| WO | 2019212804 A1 | 11/2019 |

OTHER PUBLICATIONS

Written Opinion in PCT/CN2020/098734 mailed on Mar. 25, 2021, 4 pages.
The Second Office Action in Chinese Application No. 202080101749.9 mailed on Jan. 27, 2025, 23 pages.

* cited by examiner

300

500

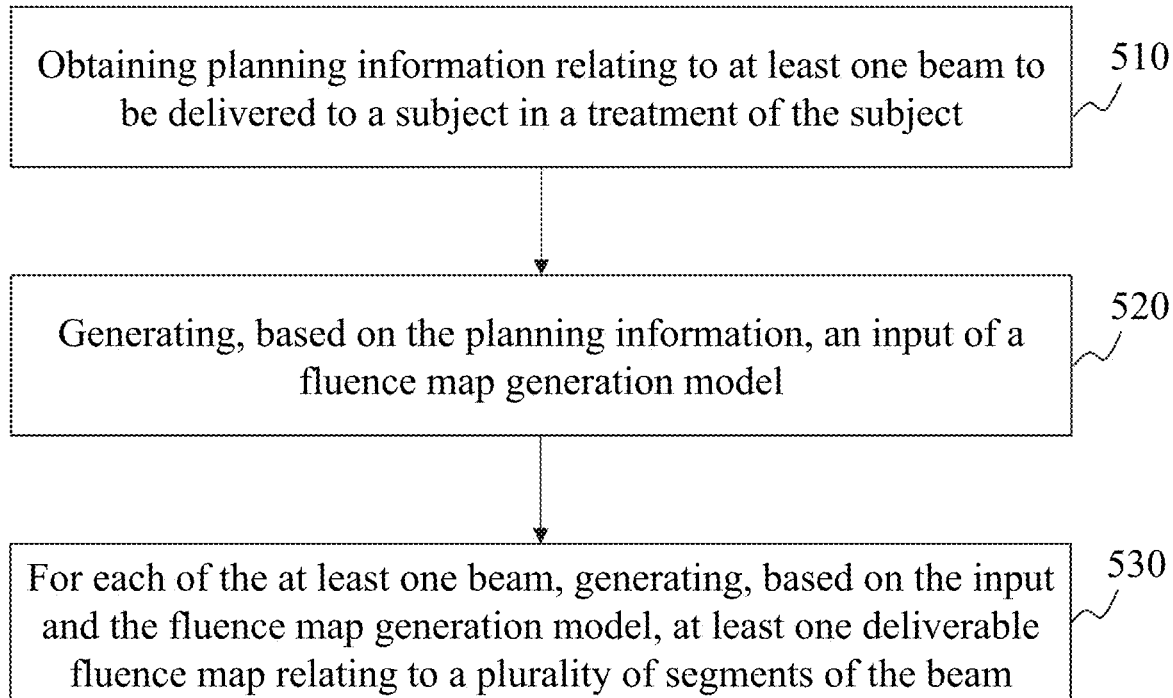

Obtaining planning information relating to at least one beam to be delivered to a subject in a treatment of the subject 510

Generating, based on the planning information, an input of a fluence map generation model 520

For each of the at least one beam, generating, based on the input and the fluence map generation model, at least one deliverable fluence map relating to a plurality of segments of the beam 530

Figure 9:
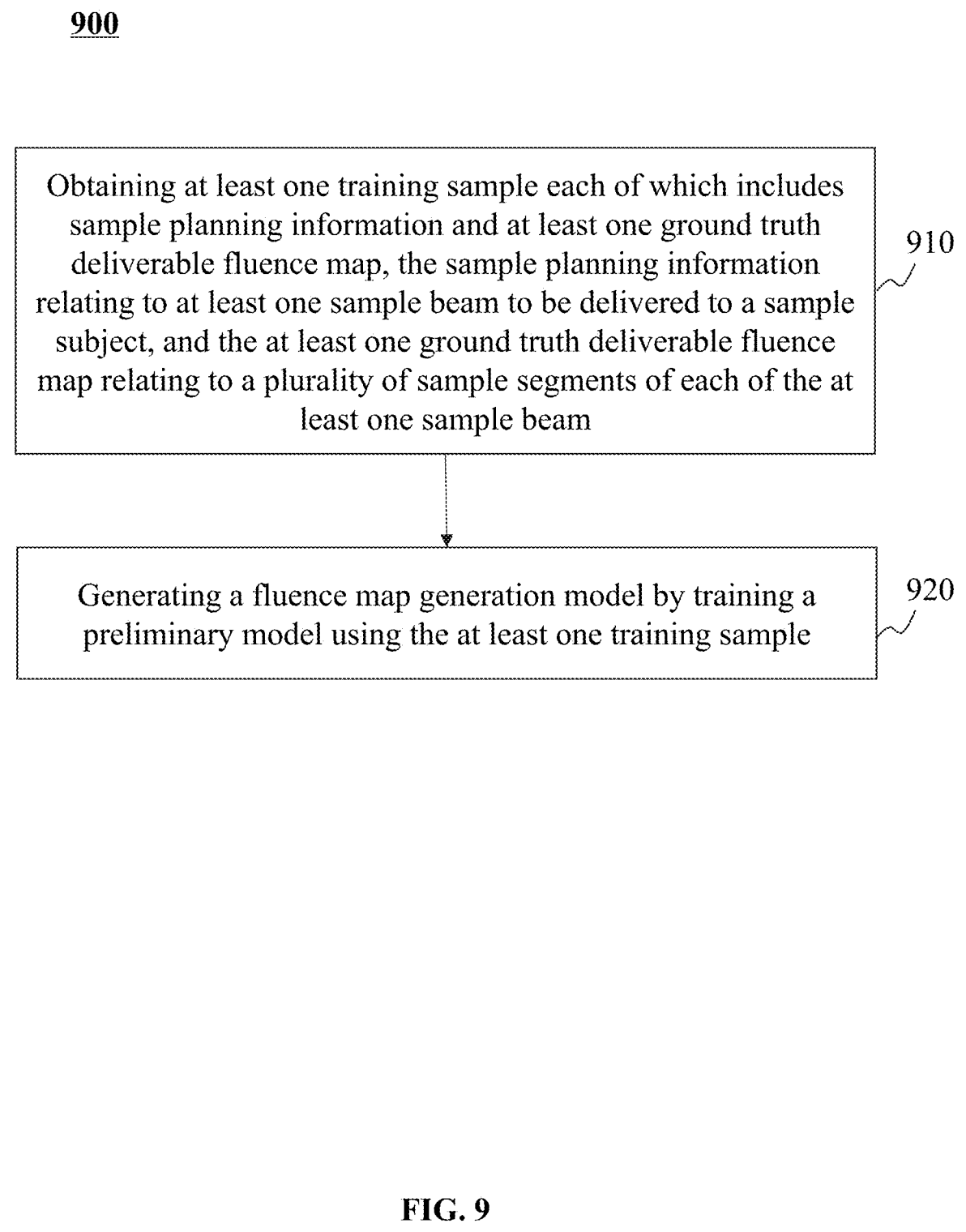

Obtaining at least one training sample each of which includes sample planning information and at least one ground truth deliverable fluence map, the sample planning information relating to at least one sample beam to be delivered to a sample subject, and the at least one ground truth deliverable fluence map relating to a plurality of sample segments of each of the at least one sample beam — 910

Generating a fluence map generation model by training a preliminary model using the at least one training sample — 920

SYSTEMS AND METHODS FOR RADIOTHERAPY PLANNING

CROSS-REFERENCE TO RELATED APPLICATIONS

This application is a continuation of International application PCT/CN2020/098734, filed on Jun. 29, 2020, the content of which is hereby incorporated by reference.

TECHNICAL FIELD

The present disclosure generally relates to radiotherapy (RT), and more particularly, systems and methods for treatment planning in radiotherapy.

BACKGROUND

Radiation therapy (or referred to as radiotherapy) has been widely employed in clinical treatment for cancers and other conditions. Before a radiation therapy, a treatment plan that describes how the radiation therapy is planned to be performed on the subject may be generated. The accuracy of the treatment plan may affect the treatment accuracy and effect of the radiation therapy.

SUMMARY

According to an aspect of the present disclosure, a system for radiotherapy planning is provided. The system may include at least one storage device including a set of instructions; and at least one processor configured to communicate with the at least one storage device. When executing the set of instructions, the at least one processor may be configured to direct the system to perform one or more of the following operations. The system may obtain planning information relating to at least one beam to be delivered to a subject in a treatment of the subject. The system may also generate an input of a fluence map generation model based on the planning information. For each of the at least one beam, the system may further generate at least one deliverable fluence map relating to at least one segment of the beam based on the input and the fluence map generation model.

In some embodiments, the planning information may include segmentation information of one or more regions of interest (ROIs) of the subject to which the beam is to be delivered, and a beam angle of each of the at least one beam.

In some embodiments, the planning information may further include a reference image of the subject.

In some embodiments, the planning information may include an optimized fluence map of each of the at least one beam.

In some embodiments, to obtain planning information relating to at least one beam to be delivered to a subject in a treatment of the subject, the system may perform the following operations. For each of the at least one beam, the system may obtain a preliminary fluence map of the beam, and generate the optimized fluence map of the beam by optimizing the preliminary fluence map.

In some embodiments, for each of the at least one beam, the at least one segment of the beam may include a plurality of segments, and the at least one deliverable fluence map relating to the plurality of segments of the beam may include a composite fluence map of the plurality of segments.

In some embodiments, for each of the at least one beam, the system may further convert the composite fluence map into a plurality of segment fluence maps each of which corresponds to one of the plurality of segments.

In some embodiments, for each of the at least one beam, the at least one deliverable fluence map relating to the at least one segment of the beam may include at least one segment fluence map each of which corresponds to one of the at least one segment.

In some embodiments, the fluence map generation model may include at least one of a convolutional neural network (CNN) or a generative adversarial network (GAN).

In some embodiments, the fluence map generation model may be generated according to a training process. The training process may include obtaining at least one training sample each of which includes sample planning information and at least one ground truth deliverable fluence map, the sample planning information relating to at least one sample beam to be delivered to a sample subject, and the at least one ground truth deliverable fluence map relating to at least one sample segment of each of the at least one sample beam. The training process may also include generating the fluence map generation model by training a preliminary model using the at least one training sample.

In some embodiments, for each of the at least one training sample, the obtaining the training sample may include one or more of the following operations. A sample preliminary fluence map of the sample beam may be obtained. A sample optimized fluence map of the sample beam may be generated by optimizing the sample preliminary fluence map. The sample optimized fluence map may be converted into at least one sample preliminary segment fluence map of the at least one sample segment of the sample beam. The at least one ground truth deliverable fluence map relating to the at least one sample segment may be generated based on the at least one sample preliminary segment fluence map.

According to an aspect of the present disclosure, a method for radiotherapy planning is provided. The method may be implemented on a computing device having at least one and at least one computer-readable storage medium for radiotherapy planning. The method may include obtaining planning information relating to at least one beam to be delivered to a subject in a treatment of the subject. The method may also include generating an input of a fluence map generation model based on the planning information. For each of the at least one beam, the method may further include generating at least one deliverable fluence map relating to at least one segment of the beam based on the input and the fluence map generation model.

According to an aspect of the present disclosure, a non-transitory computer-readable storage medium is provided. The non-transitory computer-readable storage medium may comprise a set of instructions for radiotherapy planning, wherein when executed by at least one processor, the set of instructions may direct the at least one processor to effectuate a method. The method may include obtaining planning information relating to at least one beam to be delivered to a subject in a treatment of the subject. The method may also include generating an input of a fluence map generation model based on the planning information. For each of the at least one beam, the method may further include generating at least one deliverable fluence map relating to at least one segment of the beam based on the input and the fluence map generation model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for generating at least one deliverable fluence map according to some embodiments of the present disclosure;

FIG. 9 is a flowchart illustrating an exemplary process for generating a fluence map generation model according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
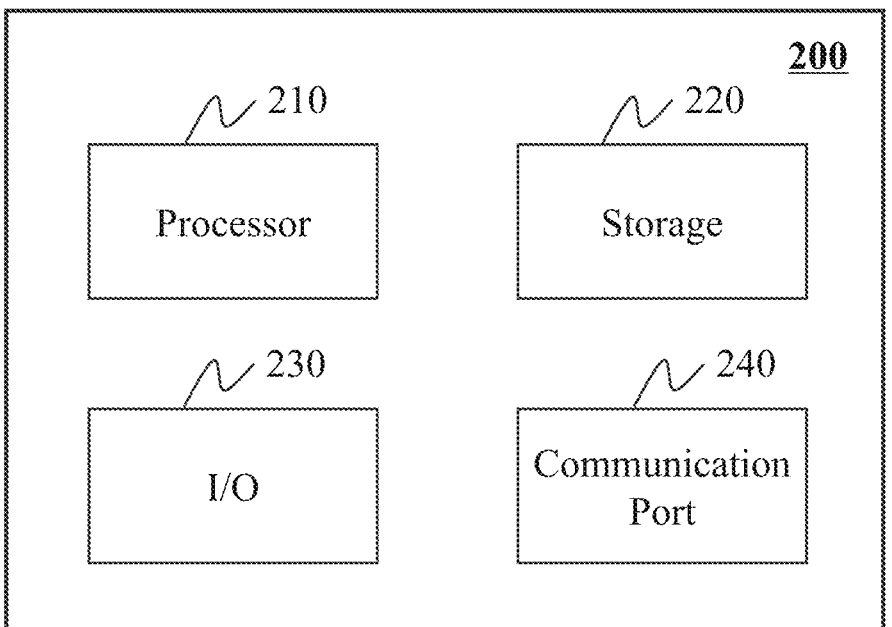
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include a radiotherapy (RT) system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a planning image, or a treatment image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

Radiotherapy has been widely employed in clinical treatment for cancers and other conditions. Treatment planning is a vital part in radiotherapy and the accuracy of a treatment plan generated by treatment planning may affect the treatment effect and/or the treatment accuracy. Normally, in a radiation treatment of a subject (e.g., a cancer patient), one or more beams, each of which includes a plurality of segments, may be delivered to the subject to treat the subject. In the treatment planning stage, one or more deliverable fluence maps that guide the delivery of the beam(s) and/or the segments of the beam(s) may need to be generated.

Conventionally, a treatment planning technique may generate a preliminary fluence map of a beam, optimize the preliminary fluence map to generate an optimized fluence map of the beam, and further divide the optimized fluence map of the beam into one or more deliverable fluence maps. The division of the optimized fluence map of the beam may often involve a generation of a plurality of preliminary segment fluence maps and an iterative or manual optimization process of the preliminary segment fluence maps. The conventional treatment planning technique may need a lot of computational resources, cause a long treatment planning time, and/or be susceptible to human errors or subjectivity.

An aspect of the present disclosure relates to systems and methods for treatment planning in radiotherapy. The systems and methods may obtain planning information relating to at least one beam to be delivered to a subject in a treatment of the subject. The systems and methods generate an input of a fluence map generation model based on the planning information. For each of the at least one beam, the systems and methods may generate at least one deliverable fluence map relating to at least one segment of the beam based on the input and the fluence map generation model. For example, the at least one deliverable fluence map of a beam may include a composite fluence map of a plurality of segments of the beam, a segment fluence map of each segment of the beam, or the like, or any combination thereof. The at least one deliverable fluence map of a beam may be used to guide the delivery of the beam during the treatment of the subject.

Compared with a conventional treatment planning technique, the systems and methods may be used to generate at least one deliverable fluence map of a beam with an improved efficiency and/or accuracy. For example, a fluence map generation model, which learns an optimal mechanism for generating deliverable fluence map(s) from training data, may be used in the treatment planning. The application of the fluence map generation model may obviate the need of generating a preliminary fluence map of the beam, optimizing the preliminary fluence map, and/or dividing the optimized fluence map, which may improve the efficiency of the treatment planning by, e.g., reducing the workload of a user, cross-user variations, and/or the time needed for the treatment planning. In addition, in some embodiments of the present disclosure, the deliverable fluence map(s) of a beam may be generated with little or no direct human intervention, which is more reliable and robust, insusceptible to human error or subjectivity, and/or fully automated.

Figure 1:
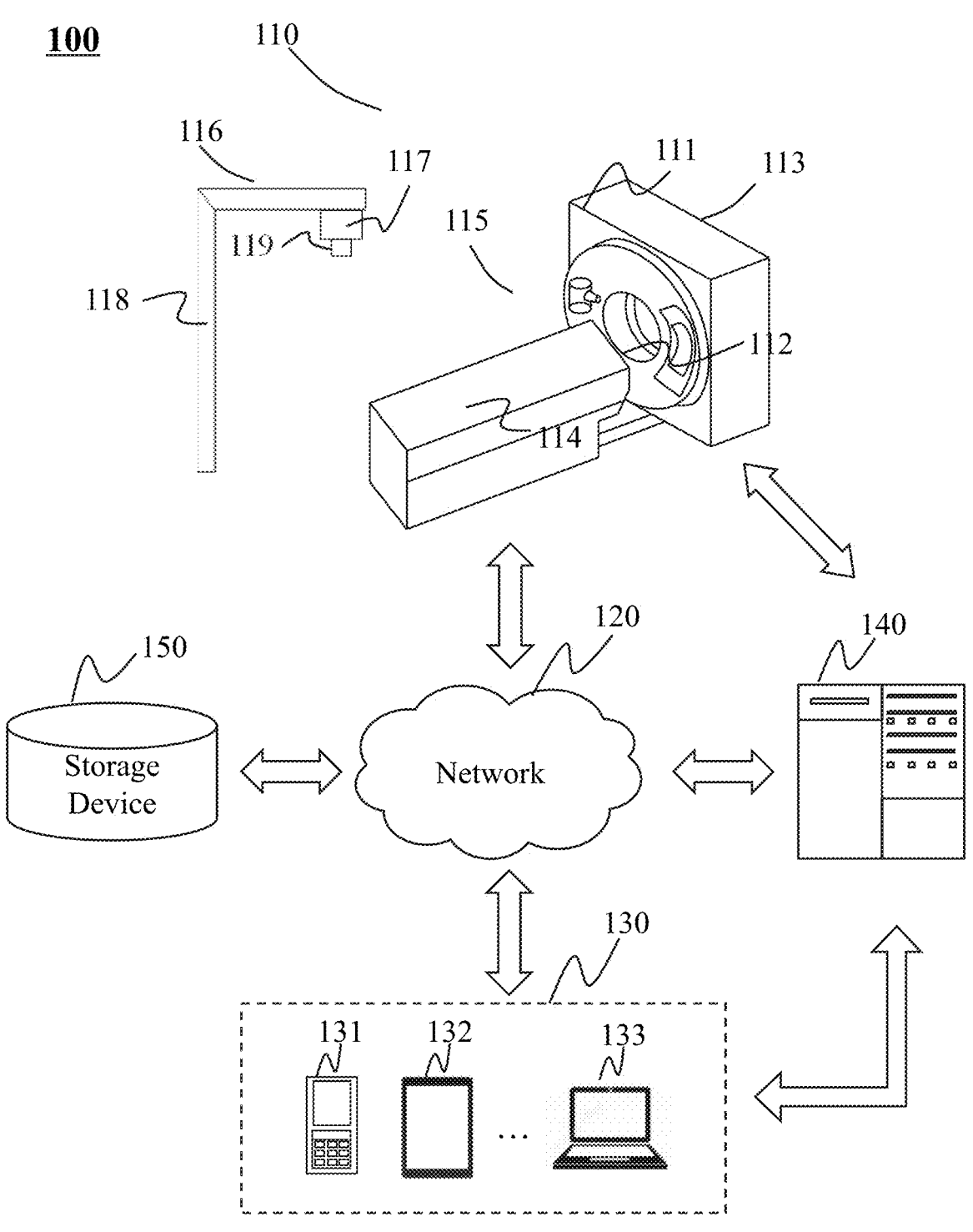
FIG. 1 is a schematic diagram illustrating an exemplary RT planning system according to some embodiments of the present disclosure.

FIG. 1 is a schematic diagram illustrating an exemplary RT planning system 100 according to some embodiments of the present disclosure. The RT planning system 100 may include a radiation delivery device 110, a network 120, one or more terminals 130, a processing device 140, and a storage device 150. In some embodiments, two or more components of the RT planning system 100 may be connected to and/or communicate with each other via a wireless connection (e.g., the network 120), a wired connection, or a combination thereof. The connection between the components of the RT planning system 100 may be variable. Merely by way of example, the radiation delivery device 110 may be connected to the processing device 140 through the network 120 or directly. As a further example, the storage device 150 may be connected to the processing device 140 through the network 120 or directly. As still another example, the terminal(s) 130 may be connected to the processing device 140 directly or through the network 120.

In some embodiments, the radiation delivery device 110 may be an RT device. The RT device may be configured to deliver a radiation treatment for cancers and other conditions. For example, the RT device may deliver one or more radiation beams to a treatment region (e.g., a tumor) of a subject (e.g., a patient) for causing an alleviation of the subject's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like.

As illustrated in FIG. 1, in some embodiments, the radiation delivery device 110 may include an imaging component 113, a treatment component 116, a couch 114, or the like. The imaging component 113 may be configured to acquire an image of a subject prior to a radiation treatment, during the radiation treatment, and/or after the radiation treatment. The subject may include any biological subject (e.g., a human being, an animal, a plant, or a portion thereof) and/or a non-biological subject (e.g., a phantom). For example, the imaging component 113 may include a computed tomography (CT) device (e.g., a cone beam computed tomography (CBCT) device, a fan-beam computed tomography (FBCT) device), an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver a radiation treatment to the subject. The treatment component 116 may include a treatment head and a gantry 118. In some embodiments, the treatment head may include a treatment radiation source 117, a collimator 119, etc. The treatment radiation source 117 may be configured to generate and emit a radiation beam toward the subject for treatment. The collimator 119 may be configured to control the shape of the radiation beam generated by the treatment radiation source 117. In some embodiments, the gantry 118 may be rotatable, and the rotation of the gantry 118 may drive the treatment head to rotate around the subject. During the rotation of gantry 118, the treatment radiation source 117 may deliver radiation beams toward the subject from different beam angles. In some embodiments, when the gantry 118 is located at a specific gantry angle, the treatment radiation source 117 may deliver a plurality of segments, which have different shapes formed by the collimator 119, toward the subject. In some embodiments, the radiation beam emitted by the treatment radiation source 117 may include electrons, photons, or other types of radiation. In some embodiments, the energy of the radiation beam may be in the megavoltage range (e.g., >1 MeV), and may be referred to as a megavoltage (MV) beam. In some embodiments, the treatment radiation source 117 may include a linear accelerator (LINAC) configured to accelerate electrons, ions, or protons.

In some embodiments, the imaging component 113 may be spaced by a distance from the treatment component 116. In some embodiments, the gantry 111 of the imaging component 113 and the gantry 118 of the treatment component 116 may share an axis of rotation. The subject may be placed on the couch 114 for treatment and/or imaging. In some embodiments, the imaging radiation source 115 and the treatment radiation source 117 may be integrated as one radiation source to image and/or treat the subject. In some embodiments, the imaging component 113 and the treatment component 116 may share a same gantry. For example, the treatment radiation source 117 may be mounted on the gantry 111 of the imaging component 113.

The network 120 may include any suitable network that can facilitate the exchange of information and/or data for the RT planning system 100. In some embodiments, one or more components of the RT planning system 100 (e.g., the radiation delivery device 110, the terminal(s) 130, the processing device 140, the storage device 150, etc.) may communicate information and/or data with one or more other components of the RT planning system 100 via the network 120. For example, the processing device 140 may obtain image data from the radiation delivery device 110 via the network 120. As another example, the processing device 140 may obtain user instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT planning system 100 may be connected to the network 120 to exchange data and/or information.

Figure 3:
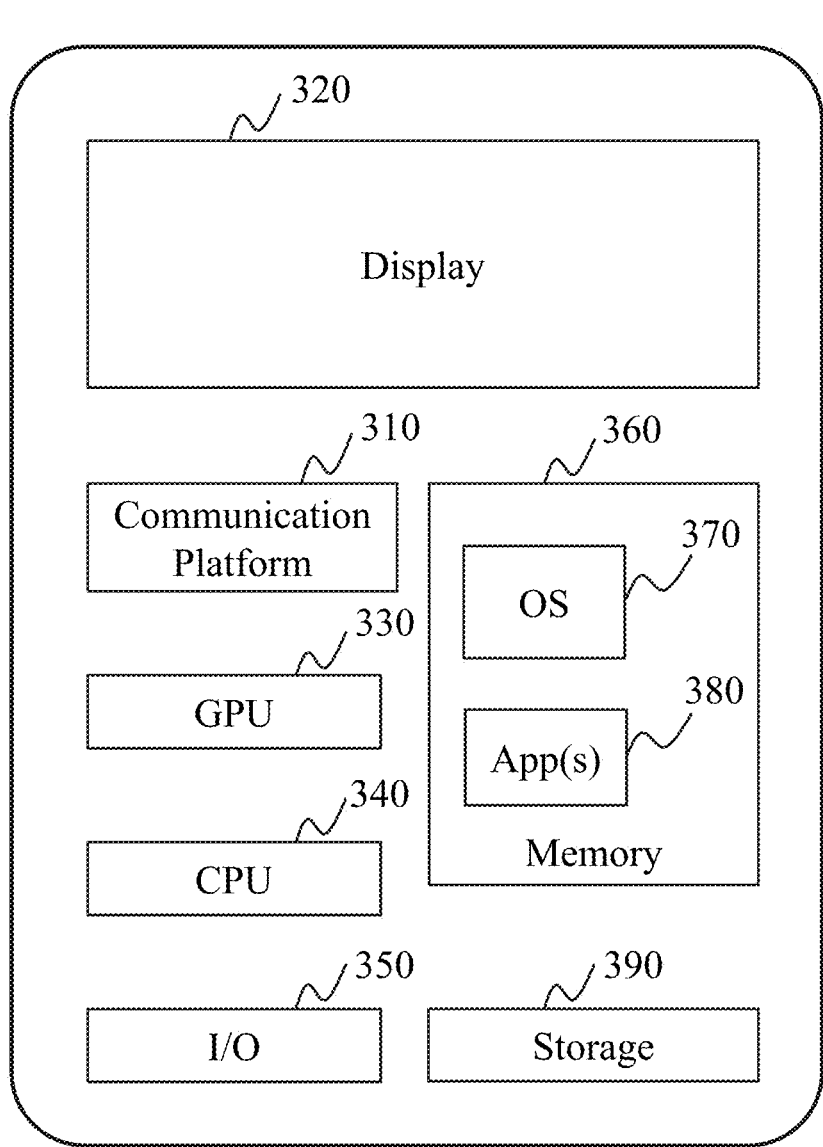
FIG. 3 is a schematic diagram illustrating exemplary hardware and/or software components of a mobile device according to some embodiments of the present disclosure.

The terminal(s) 130 may enable user interaction between a user and the RT planning system 100. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the radiation delivery device 110, the terminal(s) 130, and/or the storage device 150. For example, the processing device 140 may generate at least one deliverable fluence map by applying a fluence map generation model. As another example, the processing device 140 may generate the fluence map generation model by training a preliminary model using a plurality of training samples. In some embodiments, the generation and/or updating of the fluence map generation model may be performed on a processing device, while the application of the fluence map generation model may be performed on a different processing device. In some embodiments, the generation of fluence map generation model may be performed on a processing device of a system different from the RT planning system 100 or a server different from a server including the processing device 140 on which the application of the fluence map generation model is performed. For instance, the generation of the fluence map generation model may be performed on a first system of a vendor who provides and/or maintains such an fluence map generation model and/or has access to training samples used to generate the fluence map generation model, while fluence map generation based on the provided fluence map generation model may be performed on a second system of a client of the vendor. In some embodiments, the generation of the fluence map generation model may be performed online in response to a request for fluence map generation. In some embodiments, the generation of the fluence map generation model may be performed offline.

In some embodiments, the fluence map generation model may be generated and/or updated (or maintained) by, e.g., the manufacturer of the radiation delivery device 110 or a vendor. For instance, the manufacture or the vendor may load the fluence map generation model into the RT planning system 100 or a portion thereof (e.g., the processing device 140) before or during the installation of the radiation delivery device 110 and/or the processing device 140, and maintain or update the fluence map generation model from time to time (periodically or not). The maintenance or update may be achieved by installing a program stored on a storage device (e.g., a compact disc, a USB drive, etc.) or retrieved from an external source (e.g., a server maintained by the manufacture or vendor) via the network 120. The program may include a new model (e.g., a new fluence map generation model) or a portion of a model that substitute or supplement a corresponding portion of the original fluence map generation model.

In some embodiments, the processing device 140 may be a computer, a user console, a single server, a server group, etc. The server group may be centralized or distributed. In some embodiments, the processing device 140 may be local or remote. For example, the processing device 140 may access information stored in the radiation delivery device 110, the terminal(s) 130, and/or the storage device 150 via the network 120. As another example, the processing device 140 may be directly connected to the radiation delivery device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT planning system 100 (e.g., the processing device 140, the terminal(s) 130). One or more components of the RT planning system 100 may access the data and/or instructions stored in the storage device 150 via the network 120. In some embodiments, the storage device 150 may be directly connected to or communicate with one or more other components of the RT planning system 100 (e.g., the processing device 140, the terminal(s) 130). In some embodiments, the storage device 150 may be part of the processing device 140. In some embodiments, the storage device 150 may be connected to or communicate with the radiation delivery device 110 via the network 120, or at the backend of the processing device 140.

It should be noted that the above description of the RT planning system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the RT planning system 100 may include one or more additional components. Additionally or alternatively, one or more components of the RT planning system 100 (e.g., the imaging component 113 of the radiation delivery device 110) described above may be omitted. As another example, two or more components of the RT planning system 100 may be integrated into a single component.

FIG. 2 is a schematic diagram illustrating exemplary hardware and/or software components of a computing device 200 according to some embodiments of the present disclosure. The computing device 200 may be used to implement any component of the RT planning system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT planning system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the radiation delivery device 110, the terminal(s) 130, the storage device 150, and/or any other component of the RT planning system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the RT planning system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 140 to execute for generating at least one deliverable fluence map.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing.

Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT planning system 100. User interactions with the information stream may be achieved via the I/O 350 and provided to the processing device 140 and/or other components of the RT planning system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
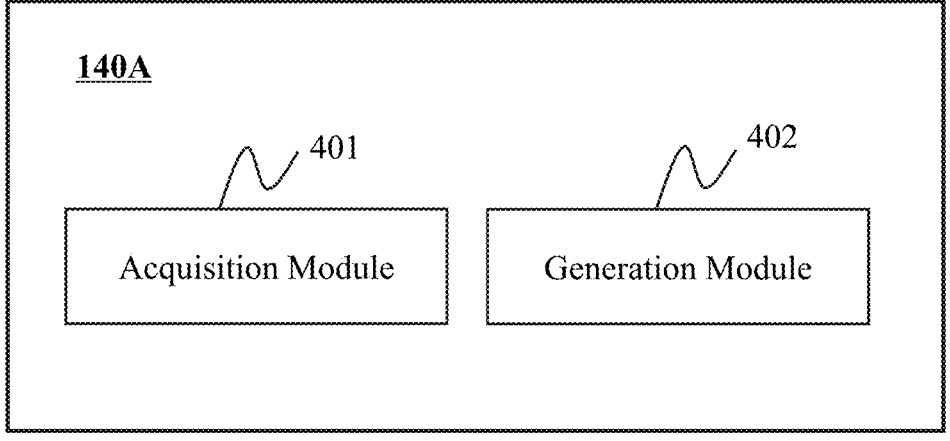
FIGS. 4A and 4B are block diagrams illustrating exemplary processing devices according to some embodiments of the present disclosure.
Figure 4B:
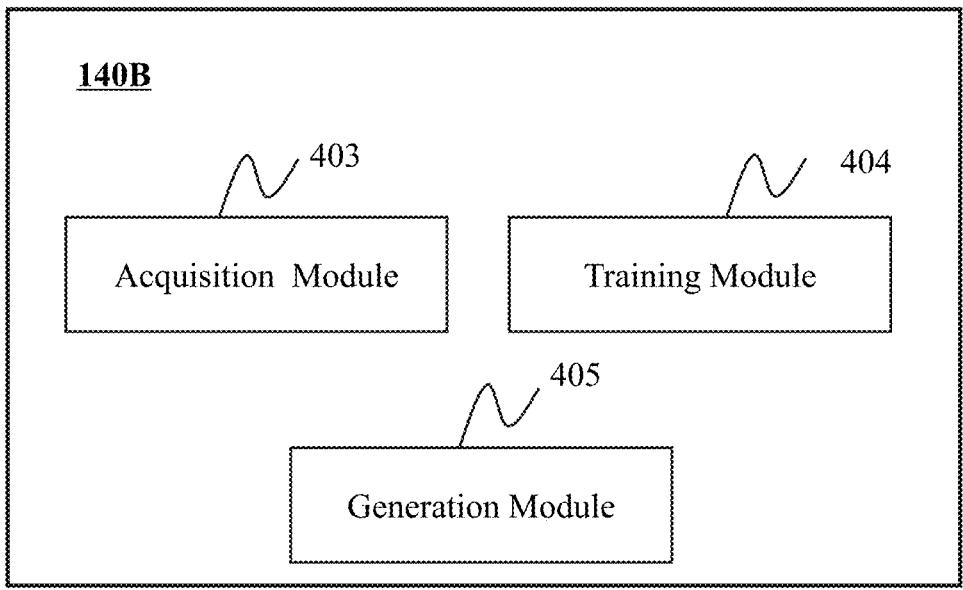

FIG. 4A and FIG. 4B are block diagrams illustrating exemplary processing devices 140A and 140B according to some embodiments of the present disclosure. In some embodiments, the processing devices 140A and 140B may be embodiments of the processing device 140 as described in connection with FIG. 1. The processing device 140A may be configured to generate one or more deliverable fluence maps for a subject to be treated. For example, the processing device 140A may apply a fluence map generation model to generate the one or more deliverable fluence maps. The processing device 140B may be configured to generate the fluence map generation model by model training.

In some embodiments, the processing devices 140A and 140B may be respectively implemented on a processing unit (e.g., the processor 210 illustrated in FIG. 2 or the CPU 340 as illustrated in FIG. 3). Merely by way of example, the processing devices 140A may be implemented on a CPU 340 of a terminal device, and the processing devices 140B may be implemented on a computing device 200. As another example, the processing device 140A may be implemented on a computing device of the RT planning system 100, while the processing device 140B may be part of a device or a system of the manufacturer of the RT planning system 100, or a portion thereof (e.g., the radiation delivery device 110). Alternatively, the processing devices 140A and 140B may be implemented on a same computing device 200 or a same CPU 340. For example, the processing devices 140A and 140B may be implemented on a same computing device 200.

As shown in FIG. 4A, the processing device 140A may include an acquisition module 401 and a generation module 402. The acquisition module 401 may be configured to obtain information relating to the RT planning system 100. For example, the acquisition module 401 may obtain planning information relating to at least one beam to be delivered to a subject in a treatment (e.g., a specific treatment session) of the subject. More descriptions regarding the obtaining of the planning information may be found elsewhere in the present disclosure. See, e.g., operation 510 and relevant descriptions thereof.

The generation module 402 may be configured to generate an input of a fluence map generation model based on planning information. As used herein, a fluence map generation model refers to a model (e.g., a machine learning model) or an algorithm configured for deliverable fluence map generation based on its input. More descriptions regarding the generation of the input of the fluence map generation model may be found elsewhere in the present disclosure. See, e.g., operation 520 and relevant descriptions thereof. Additionally or alternatively, the generation module 402 may be configured to generate at least one deliverable fluence map relating to the at least one beam based on the input and the fluence map generation model. More descriptions regarding the generation of the at least one deliverable fluence map may be found elsewhere in the present disclosure. See, e.g., operation 530 and relevant descriptions thereof.

As shown in FIG. 4B, the processing device 140B may include an acquisition module 403, a training module 404, and a generation module 405.

The acquisition module 403 may be configured to obtain information relating to the training of the fluence map generation model. For example, the acquisition module 403 may obtain at least one training sample each of which may include sample planning information and at least one ground truth deliverable fluence map. The sample planning information of a training sample may relate to at least one sample beam to be delivered to a sample subject. More descriptions regarding the acquisition of a training sample may be found elsewhere in the present disclosure. See, e.g., operation 910 and relevant descriptions thereof.

The training module 404 may be configured to generate the fluence map generation model by training a preliminary model using the at least one training sample. More descriptions regarding the generation of the fluence map generation model may be found elsewhere in the present disclosure. See, e.g., operation 920 and relevant descriptions thereof.

The generation module 405 may be configured to generate at least one ground truth deliverable fluence map of a training sample. For example, the generation module may generate at least one ground truth deliverable fluence map of a training sample by performing one or more operations of process 1000 as described in connection with FIG. 10.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and the processing device 140B may share two or more of the modules, and any one of the modules may be divided into two or more units. For instance, the processing devices 140A and 1406 may share a same acquisition module, that is, the acquisition module 401 and the acquisition module 403 are a same module. In some embodiments, the processing device 140A and/or the processing device 140B may include one or more additional modules, such as a storage module (not shown) for storing data. In some embodiments, the processing device 140A and the processing device 140B may be integrated into one processing device 140.

FIG. 5 is a flowchart illustrating an exemplary process for generating at least one deliverable fluence map for a subject to be treated according to some embodiments of the present disclosure. In some embodiments, process 500 may be executed by the RT planning system 100. For example, the process 500 may be implemented as a set of instructions (e.g., an application) stored in a storage device (e.g., the storage device 150, the storage device 220, and/or the storage 390). In some embodiments, the processing device 140A (e.g., the processor 210 of the computing device 200, the CPU 340 of the mobile device 300, and/or one or more modules illustrated in FIG. 4A) may execute the set of instructions, and when executing the instructions, the processing device 140A may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

Conventionally, before (e.g., days or weeks before) a radiation treatment is performed on the subject, a planning image of the subject may be acquired by an imaging device (e.g., a CT device, an MRI device), and a treatment plan of the subject may be generated according to the planning image. The treatment plan may describe how the radiation treatment is planned to be performed on the subject. Merely by way of example, the radiation treatment may be delivered to the subject during several treatment sessions, spread over a treatment period of multiple days (e.g., 2 to 5 weeks). The treatment plan may include information including, e.g., how one or more beams are delivered to a target of the subject during each treatment session over the course of treatment. For example, the treatment plan may provide a total dose (e.g., 0.1 Gy, 10 Gy, 50 Gy, 100 Gy, etc.) and a dose distribution in the subject during each treatment session.

In some embodiments, during a treatment (e.g., a treatment session) of the subject, at least one beam may be delivered to the subject by a radiotherapy device from a specific beam angle (or a treatment angle) to treat the subject. Each beam may be delivered to the subject by delivering at least one segment toward the subject. For example, a plurality of segments (or fields) may be delivered toward the subject in sequence. The plurality of segments corresponding to a beam may have different shapes formed by a collimator (e.g., a multi-leaf collimator (MLC)) of the radiotherapy device. In the treatment planning stage, a preliminary fluence map (or referred to as a planning fluence map) corresponding to each beam may be generated. The preliminary fluence map of a beam may indicate a planned distribution of radiation dose to be delivered to the subject by all the at least one segment of the beam. For illustration purposes, the following descriptions describe the delivery of a beam by a plurality of segments of the beam. It should be understood that this is not intended to be limiting, and a beam may include only one segment.

Conventionally, the preliminary fluence map of a beam may need to be optimized to generate an optimized fluence map of the beam. For example, a fluence map optimization algorithm may be utilized to optimize the preliminary fluence map so as to generate an optimized fluence map with a higher quality (e.g., a higher resolution, a lower radiation dose on healthy organs, and/or a more uniform dose distribution within a target of the subject) than the preliminary fluence map. Exemplary fluence map optimization algorithms may include a linear/nonlinear programming algorithm, a mixed-integer programming algorithm, a simulated annealing algorithm, a genetic algorithm, a fluence map optimization (FMO) algorithm, a Direct Aperture Optimization (DAO) algorithm, a Direct Machine Parameter Optimization (DMPO) algorithm, etc.

The optimized fluence map of the beam may then be divided into a plurality of segments (or referred to as deliverable apertures) according to, for example, a leaf sequencing algorithm. For each of the segments, a preliminary segment fluence map may be used to describe a planned distribution of radiation dose to be delivered to the subject by the segment. However, an error may exist between the optimized fluence map and a preliminary composite fluence map of the preliminary segment fluence maps of the plurality of segments due to, for example, limitations of mathematical operations performed in the generation of the optimized fluence map and/or the preliminary segment fluence maps. The error between the optimized fluence map and the preliminary composite fluence map may affect the accuracy of the treatment planning. Conventional treatment planning techniques may need to optimize the preliminary segment fluence maps of the segments to generate optimized segment fluence maps that can be used for guiding the delivery of the segments. For example, the preliminary segment fluence maps may be optimized iteratively so that an optimized composite fluence map of the optimized segment fluence maps may match the optimized fluence map. As another example, a user (e.g., a doctor, a radiologist) may manually adjust parameter(s) of the segments and/or the preliminary segment fluence maps via, e.g., an interface implemented on a terminal device. The optimization of the preliminary segment fluence maps may need a lot of computational resources, cause a long treatment planning time, and/or be susceptible to human errors or subjectivity.

It is desirable to provided systems and methods for generating at least one deliverable fluence map for a beam to be delivered to the subject. As used herein, a deliverable fluence map of a beam refers to a fluence map that can be used to guide the delivery of the beam in the radiation treatment. For example, the at least one deliverable fluence map of a beam may include a plurality of segment fluence maps (or referred to as optimized segment fluence maps as aforementioned) each of which corresponds to one of a plurality of segments of the beam. As another example, the at least one deliverable fluence map may include a composite fluence map (or referred to as an optimized composite fluence map as aforementioned) of the plurality of segments.

For example, the process 500 described below may be used to generate at least one deliverable fluence map for a beam to be delivered to the subject by applying a fluence map generation model. A fluence map generation model refers to a model (e.g., a machine learning model) or an algorithm configured for deliverable fluence map generation based on its input. Compared with a conventional way that needs to generate a plurality of preliminary segment fluence maps of the beam and optimize the preliminary segment fluence maps iteratively or manually, the systems and methods disclosed herein may be more efficient and accurate by, e.g., obviating the need of segment fluence map optimization, reducing the workload of a user, cross-user variations, and the time needed for the generation of the at least one deliverable fluence map.

Figure 11:
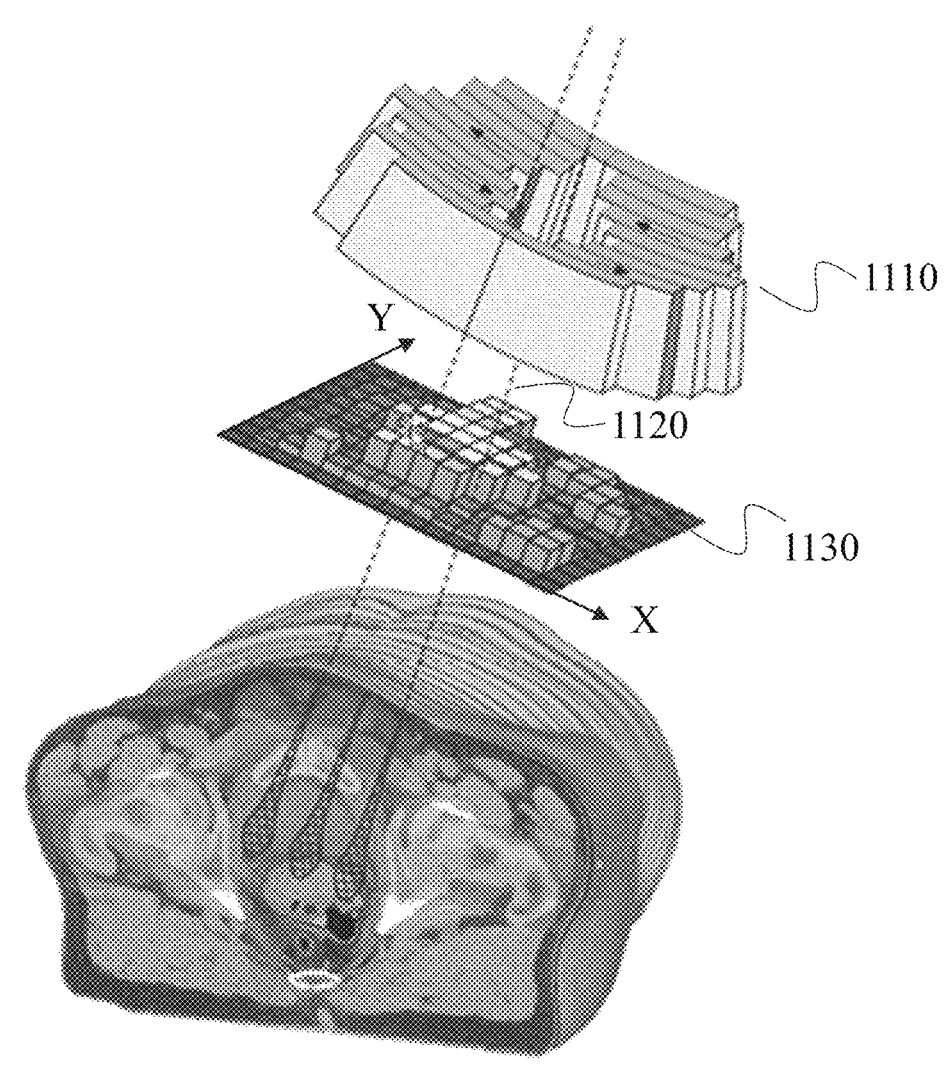
FIG. 11 is a schematic diagram illustrating an exemplary segment fluence map of a segment of a beam according to some embodiments of the present disclosure.

As used herein, a fluence map of a beam or one or more segments of the beam may be represented in the form of, for example, a map, a graph, a table, or the like. For illustration purposes, FIG. 11 illustrates an exemplary segment fluence map 1130 of a segment 1120 of a beam according to some embodiments of the present disclosure. The segment 1120 of the beam may be modulated by an MLC 1110 of a radiotherapy device. As shown in FIG. 11, the segment fluence map 1130 may be represented in a two-dimensional graph that indicates the distribution of radiation dose on a plane perpendicular to an incidence direction of the segment 1120 (e.g., a direction of a central axis of the beam). The two-dimensional graph may include an X-axis corresponding to a horizontal direction of the plane and a Y-axis corresponding to a vertical direction of the plane. A point in the segment fluence map 1130 may correspond to a physical point or region on the plane. The X-axis and Y-axis coordinates of a point in the segment fluence map 1130 may reflect the position of the corresponding physical point or region in the horizontal direction and the vertical direction of the plane, respectively. The value of a point in the segment fluence map 1130 may reflect an intensity of photons irradiated on the corresponding physical point or region (i.e., a radiation dose at the physical point or region. It should be noted that the segment fluence map 1130 illustrated in FIG. 11 is provided for illustration purposes, and not intended to be limiting. The form of the segment fluence map 1130 may be modified according to an actual need. For example, different points in the segment fluence map 1130 may be displayed in different colors according to the values of the points.

In 510, the processing device 140A (e.g., the acquisition module 401) may obtain planning information relating to at least one beam to be delivered to the subject in a treatment (e.g., a specific treatment session) of the subject.

The subject may include a patient, a portion of the patient, or any organism that needs to be treated by a radiotherapy device (e.g., the radiation delivery device 110). The planning information may include any information relating to the at least one beam to be delivered to the subject. For example, the planning information may include feature information (e.g., the gender, the age, the height, the thickness, etc.) of the subject, feature information of one or more regions of interest (ROIs) of the subject, a beam angle of each of the at least one beam, a reference image of the subject, a preliminary fluence map of each of the at least one beam, an optimized fluence map of each of the at least one beam, a dose constrain relating to the at least one beam, a prescription of the subject prescribed by a user (e.g., a doctor, a radiologist), or the like, or any combination thereof.

The ROI(s) of the subject may include a target and/or an organ at risk (OAR) near the target. The target may include a region of the subject including at least part of malignant tissue (e.g., a tumor, a cancer-ridden organ, or a non-cancerous target of radiation therapy). For example, the target may be a tumor, an organ with a tumor, a tissue with a tumor, or any combination thereof, that needs to be treated by radiation. The OAR may include an organ and/or a tissue that are close to the target and not intended to be subjected to radiation, but under the risk of radiation damage due to its proximity to the target. Exemplary feature information of an ROI of the subject may include a position, a contour, a shape, a height, a width, a thickness, an area, a ratio of height to width, or the like, or any combination thereof, of the ROI.

In some embodiments, the feature information of an ROI may include segmentation information (or referred to as contour information or edge information) of the ROI. The segmentation information of the ROI may include, for example, a contour of the ROI segmented from the reference image (or another image) of the subject, one or more parameters indicating the contour of the ROI (e.g., the shape, the height, the width, the thickness, the area, the ratio of height to width), or the like, or any combination thereof. More descriptions regarding the segmentation information may be found elsewhere in the present disclosure. See, e.g., FIG. 6 and relevant descriptions thereof.

The beam angle of a beam refers to an angle or direction from which of the segments of the beam are delivered to the subject in the process of radiotherapy. The reference image of the subject may be a two-dimensional (2D) image, a three-dimensional (3D) image, a four-dimension (4D) image (e.g., a time series of 3D images), or the like, or a combination thereof. The reference image of the subject may include a CT image (e.g., a cone beam CT (CBCT) image, a fan beam CT (FBCT) image), an MR image, a PET image, an X-ray image, a fluoroscopy image, an ultrasound image, a radiotherapy radiographic image, a SPECT Image, or the like, or a combination thereof. In some embodiments, the reference image of the subject may be a planning image (e.g., a CT image) according to which the treatment plan is made. The dose constrain relating to the at least one beam may include, for example, a maximum total radiation dose delivered to the subject or a portion thereof (e.g., the target, an OAR) by the at least one beam, a maximum radiation dose delivered to the subject (or a portion thereof) by each beam, a maximum radiation dose delivered to the subject (or a portion thereof) by each segment of each beam, or the like, or any combination thereof. In some embodiments, the total radiation dose delivered to the subject by all the at least one beam may need to satisfy specific constrain(s) (e.g., lower than a threshold value). The prescription of the subject may be provided by a user (e.g., a doctor or a radiologist), which may include a tumor location, a grade of a tumor, a maximum total radiation dose, the position of a radiation area, or other information provided by the user, or any combination thereof.

In some embodiments, the planning information (or a portion thereof) may be previously generated and stored in a storage device (e.g., the storage device 150, the storage device 220, or an external storage device). The processing device 140A may obtain the planning information (or a portion thereof) from the storage device. For example, the reference image of the subject may be a historical medial image of the subject stored in the storage device, and the processing device 140A may retrieve the historical medical image from the storage device as the reference image. Alternatively, the processing device 140A may cause an imaging device (e.g., the imaging component 113) to acquire the reference image by scanning the subject and obtain the reference image of the subject from the imaging device.

In some embodiments, the planning information (or a portion thereof) may be generated by the processing device 140A. Merely by way of example, for each of the at least one beam, the processing device 140A may obtain a preliminary fluence map of the beam, and optimize the preliminary fluence map to generate the optimized fluence map of the beam. The optimized fluence map of each of the at least one beam may be regarded as the planning information relating to the at least one beam. In some embodiments, the processing device 140A may optimize a preliminary fluence map according to a fluence map optimization algorithm as described elsewhere in this disclosure.

In 520, the processing device 140A (e.g., the generation module 402) may generate an input of a fluence map generation model based on the planning information.

As used herein, a fluence map generation model refers to a model (e.g., a machine learning model) or an algorithm configured for deliverable fluence map generation based on its input. In some embodiments, the fluence map generation model may be a machine learning model. For example, the fluence map generation model may include a neural network model, such as a convolutional neural network (CNN) model (e.g., a full CNN model, V-net model, a U-net model, an AlexNet model, an Oxford Visual Geometry Group (VGG) model, a ResNet model), a generative adversarial network (GAN) model, or the like, or any combination thereof. In some embodiments, the fluence map generation model may include one or more components for feature extraction and/or feature combination, such as a fully convolutional block, a skip-connection, a residual block, a dense block, or the like, or any combination thereof.

In some embodiments, the processing device 140A may obtain the fluence map generation model from one or more components of the RT planning system 100 (e.g., the storage device 150, the terminals(s) 130) or an external source via a network (e.g., the network 120). For example, the fluence map generation model may be previously trained by a computing device (e.g., the processing device 140B), and stored in a storage device (e.g., the storage device 150, the storage device 220, and/or the storage 390) of the RT planning system 100. The processing device 140A may access the storage device and retrieve the fluence map generation model from the storage device. In some embodiments, the fluence map generation model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the fluence map generation model may be a supervised learning algorithm, a semi-supervised learning algorithm, an unsupervised learning algorithm, or the like. In some embodiments, the fluence map generation model may be generated by a computing device (e.g., the processing device 140B) by performing a process (e.g., process 900) for generating a fluence map generation model disclosed herein.

In some embodiments, the input of the fluence map generation model may include the reference image of the subject, the segmentation information of the ROI(s) of the subject, and the beam angle of each of the at least one beam. Alternatively, the input of the fluence map generation model may include the optimized fluence map of each of the at least one beam. In some embodiments, the at least one beam may include a plurality of beams. The processing device 140A may separately determine an input for each of the beams based on the planning information. Merely by way of example, for each of the beams, the processing device 140A may obtain or generate a reference image, segmentation information of the ROI(s), and a beam angle of the beam as the input corresponding to the beam. Alternatively, the plurality of beams may share the same input. Merely by way of example, the processing device 140A may obtain or generate the optimized fluence maps of the plurality of beams as an input corresponding to the beams. More descriptions regarding the input of the fluence map generation model may be found elsewhere in the present disclosure. See, e.g., FIGS. 6 to 8 and relevant descriptions thereof.

In 530, for each of the at least one beam, the processing device 140A (e.g., the generation module 402) may generate at least one deliverable fluence map relating to the plurality of segments of the beam based on the input and the fluence map generation model.

As aforementioned, the at least one deliverable fluence map relating to the segments of a beam may include, for example, a composite fluence map of the plurality of segments, a segment fluence map of each of the segments, or the like, or any combination thereof. In some embodiments, the processing device 140A may input the input determined in 520 into the fluence map generation model, and the fluence map generation model may output the at least one deliverable fluence map of each beam in response to the input. For example, for a beam, the fluence map generation model may output a composite fluence map of the segments of the beam or a plurality of segment fluence maps each of which corresponds to one of the segments of the beam. In some embodiments, the beam may include only one segment, and the at least one deliverable fluence map of the beam may include a segment fluence map of the segment.

Alternatively, the fluence map generation model may generate an output in response to the input, and the processing device 140A may generate the at least one deliverable fluence map for a beam based on the output of the fluence map generation model. For example, the output of the fluence map generation model may include a composite fluence map of a beam, the processing device 140A may convert the composite fluence map into a plurality of segment fluence maps the plurality of segments of the beam according to, for example, a leaf sequencing algorithm.

In some embodiments, the at least one beam may include a plurality of beams. In 520, the processing device 140A may determine an input corresponding to each of the beams. In 530, for each of the beams, the processing device 140A may input the corresponding input into the fluence map generation model to obtain the at least one deliverable fluence map of the beam, or obtain an output from the fluence map generation model and generate the at least one deliverable fluence map of the beam based on the output. Alternatively, the plurality of beams may share a same input. The processing device 140A may input the input into the fluence map generation model, and the fluence map generation model may jointly output the at least one deliverable fluence map of each beam. More descriptions regarding the generation of the at least one deliverable fluence map of each beam may be found elsewhere in the present disclosure. See, e.g., FIGS. 6 to 8 and relevant descriptions thereof.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional operation before 510 to obtain one or more optimized fluence maps relating to the at least one beam.

Figure 6:
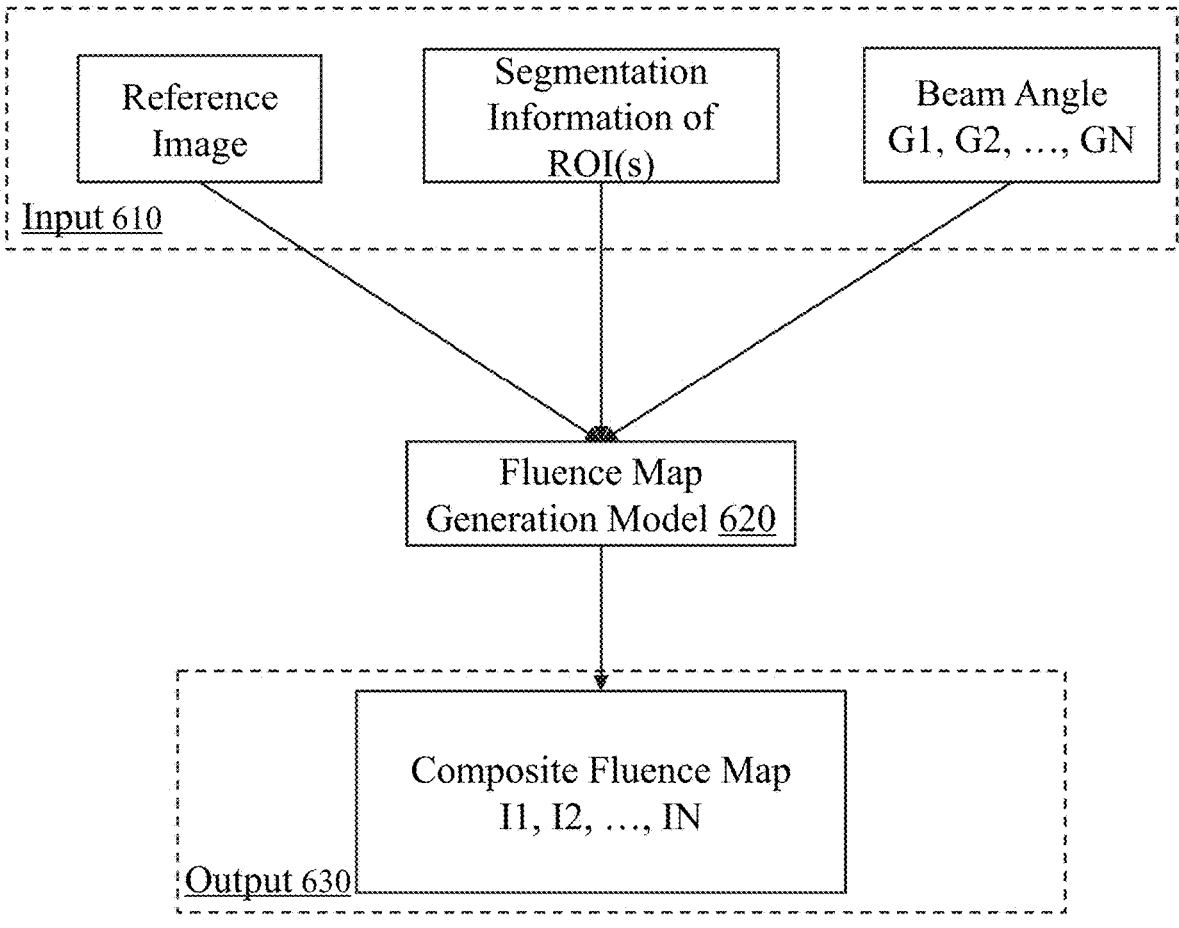
FIG. 6 is a schematic diagram illustrating an exemplary fluence map generation model according to some embodiments of the present disclosure.

FIG. 6 is a schematic diagram illustrating an exemplary fluence map generation model 620 according to some embodiments of the present disclosure.

As shown in FIG. 6, an input 610 of the fluence map generation model 620 may include a reference image of a subject, segmentation information of one or more ROIs of the subject, and a beam angle of each beam to be delivered to the subject during a treatment. For illustration purposes, it is assumed that N beam(s) may be delivered to the subject during the treatment, wherein N may be any positive integer. In such cases, N beam angle(s) (denoted as G1, G2, . . . , and GN) of the N beam(s) may be obtained as part of the input 610.

As described in connection with 510, the segmentation information of an ROI may include a contour of the ROI segmented from the reference image (or another image) of the subject, one or more parameters indicating the contour of the ROI (e.g., the shape, the height, the width, the thickness, the area, the ratio of height to width), or the like, or any combination thereof.

In some embodiments, the contour of an ROI may be segmented from the reference image (or another image) of the subject manually, semi-automatically, or automatically. In a manual approach, the contour of the ROI may be segmented from the reference image (or another image) according to an instruction provided by a user. For example, via a user interface implemented on, e.g., a terminal 130 or a mobile device 300, a user may mark the contour of the ROI in the reference image. In a semi-automatic approach, the contour of the ROI may be identified from the reference image (or another image) by a computing device (e.g., the computing device 200 as illustrated in FIG. 2) with user intervention. For example, the contour segmentation may be performed by the computing device based on an image segmentation algorithm in combination with information provided by a user. Exemplary user intervention in a semi-automatic approach for the contour segmentation may include providing a parameter relating to the image segmentation algorithm, providing position parameter(s) relating to the ROI, making an adjustment to or confirming a preliminary contour segmentation performed by the computing device, providing instructions to cause the computing device to repeat or redo the contour segmentation, etc. In an automatic approach, the contour of the ROI may be identified from the reference image automatically by a computing device (e.g., the computing device 200 as illustrated in FIG. 2) without user intervention. For example, the contour may be identified from the reference image automatically by image analysis, for example, according to an image segmentation algorithm, a feature identification algorithm, or the like, or any combination thereof.

In some embodiments, the input 610 may be inputted into the fluence map generation model 620 directly. Alternatively, the input 610 may be preprocessed and the preprocessed input may be inputted into the fluence map generation model 620. For example, the processing device 140A may perform one or more image processing operations, such as an image denoising, an image enhancement, an image smoothing, an image transformation, an image resampling, an image normalization, or the like, or any combination thereof, on the reference image to preprocess the reference image. Merely by way of example, the processing device 140A may determine whether the image resolution of the reference image is the same (or substantially same) as a preset image resolution. If the reference image has an imaging resolution different from the preset image resolution, the processing device 140A may resample the reference image to generate a resampled reference image having the preset image resolution.

The output 630 of the fluence map generation model 620 may include composite fluence map(s) (denoted as I1, I2, . . . , and IN) each of which corresponds to one of the N beam(s). For example, the composite fluence map Ii may correspond to a plurality of segments of the beam having the beam angle Gi, wherein i may be any positive integer equal to or smaller than N. In some embodiments, the composite fluence map Ii may be converted into a plurality of segment fluence maps each of which corresponds to one of the segments of the $i^{th}$ beam according to, for example, a leaf sequencing algorithm.

In some embodiments, N may be greater than 1, and a plurality of beams may be planned to be delivered to the subject during the treatment. The input 610 of the fluence map generation model 620 may include an input corresponding to each of the beams. For each of the beams, the corresponding input may be inputted into the fluence map generation model 620 to obtain the composite fluence map of the segments of the beam. For example, for the $i^{th}$ beam, the corresponding input may include the reference image of the subject, the segmentation information of the ROI(s) of the subject, and the beam angle Gi of the $i^{th}$ beam. The input of the $i^{th}$ beam may be inputted into the fluence map generation model 620, and the fluence map generation model 620 may output the composite fluence map Ii corresponding to the $i^{th}$ beam.

In some embodiments, the plurality of beams may share the same input 610, which includes the reference image, the segmentation information of the ROI(s), and the beam angle of each of the beams. The input 610 may be inputted into the fluence map generation model 620, and the fluence map generation model 620 may jointly output the composite fluence maps of the beams. In some embodiments, the fluence map generation model 620 may be trained to learn an interaction or a relationship between the beams. For example, during the treatment, the total radiation dose delivered to the subject by all the beams may need to satisfy specific constrain(s), e.g., be lower than a threshold dose. The radiation doses delivered by different beams may have a compensatory relationship, e.g., if the radiation dose delivered by a certain beam is relatively high, the radiation dose delivered by the remaining beam(s) may be relatively low. In the generation of the composite fluence maps of the beams, the fluence map generation model 620 may take the compensatory relationship between the beams into consideration, which may prevent the subject from radiation damage and improve the treatment accuracy. In some embodiments, the fluence map generation model 620 may learn the compensatory relationship from training data. Alternatively, the training data of the fluence map generation model 620 may include one or more parameters relating to the compensatory relationship, such as the threshold dose with respect to the total radiation dose delivered by the beams. Optionally, in the application of the fluence map generation model 620, the threshold dose may be part of the input 610.

In some embodiments, a plurality of fluence map generation models 620, each of which corresponds to a specific portion (e.g., a specific organ) of humans, may be available. The processing device 140A may select a fluence map generation model 620 from the plurality of fluence map generation models 620 according to, for example, the target of the subject to be treated. The selected fluence map generation model 620 may be utilized in the treatment planning for the subject. Merely by way of example, a first fluence map generation model 620 corresponding to the heart, a second fluence map generation model 620 corresponding to the abdomen, and a third fluence map generation model 620 corresponding to the head may be available. If the target is in the head of the subject, the processing device 140A may select the third fluence map generation model 620 for generating deliverable fluence map(s) for the subject.

As described elsewhere in this disclosure (e.g., FIG. 5 and the relevant descriptions), a conventional treatment planning technique may need to generate a preliminary fluence map of a beam, optimize the preliminary fluence map to generate an optimized fluence map of the beam, and further divide the optimized fluence map of the beam into deliverable apertures. The division of the optimized fluence map of the beam may often involve an iterative or manual optimization process of a plurality of preliminary segment fluence maps. According to some embodiments of the present disclosure, the reference image in combination with other information may be inputted the fluence map generation model 620 for generating at least one deliverable fluence map of a beam. The application of the fluence map generation model 620 may obviate the need of generating the preliminary fluence map of the beam, optimizing the preliminary fluence map, and dividing the optimized fluence map, which may improve the efficiency of the treatment planning by, e.g., reducing the workload of a user, cross-user variations, and/or the time needed for the treatment planning. In addition, in some embodiments, a specific fluence map generation model 620 may be selected according to the target of the subject and used in the treatment planning. Compared with using a same fluence map generation model for different targets, the systems and methods disclosed herein may improve the accuracy of the generated at least one deliverable fluence map, which in turn, the treatment accuracy.

Figure 7:
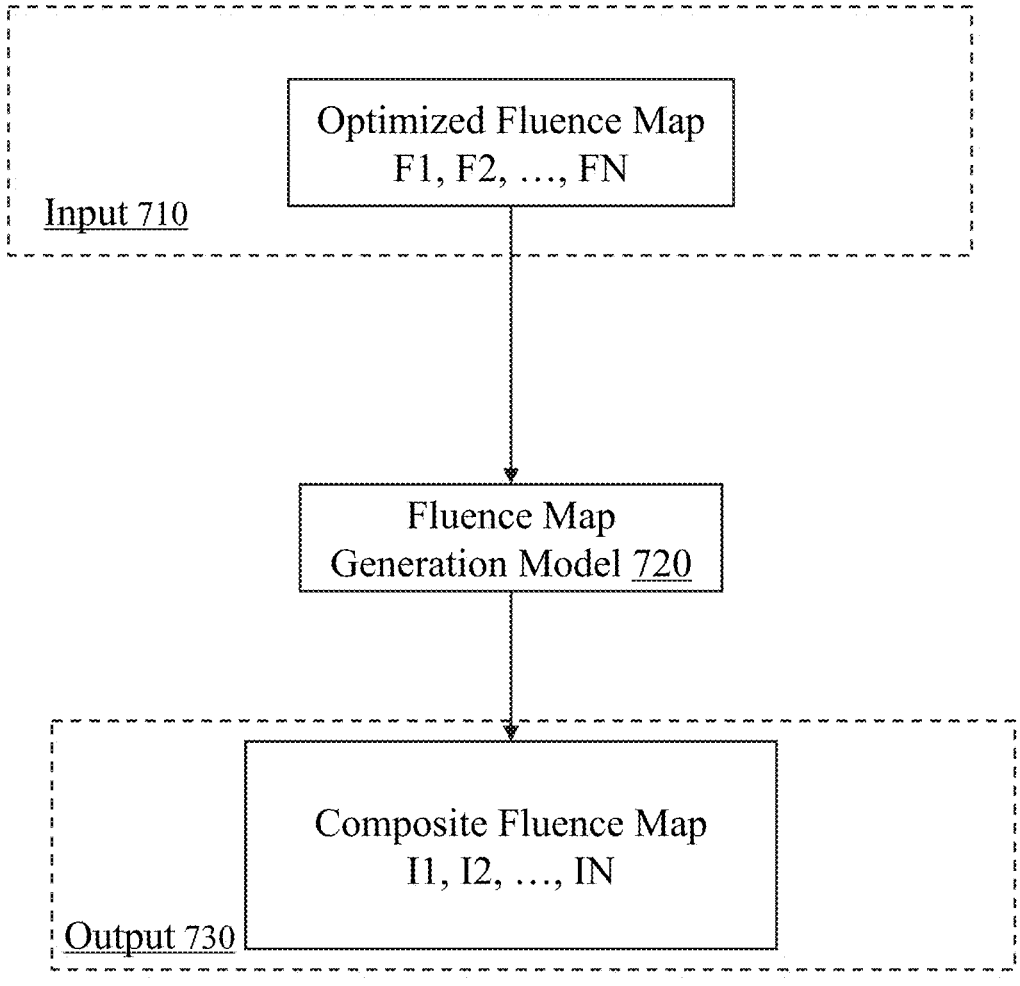
FIG. 7 is a schematic diagram illustrating an exemplary fluence map generation model according to some embodiments of the present disclosure.

FIG. 7 is a schematic diagram illustrating an exemplary fluence map generation model 720 according to some embodiments of the present disclosure.

As shown in FIG. 7, an input 710 of the fluence map generation model 720 may include an optimized fluence map of each of the at least one beam to be delivered to the subject. For example, N beam(s) may be delivered to the subject, N optimized fluence map(s) (denoted as F1, F2, . . . , and FN) may be designated as the input 710. In some embodiments, for each beam, the optimized fluence map of the beam may be generated by the processing device 140A by optimizing a preliminary fluence map of the beam. For example, the preliminary fluence map of the beam may be generated based on a planning image (e.g., a CT image)

of the subject, and the processing device 140A may optimize the preliminary fluence map based on a fluence map optimization algorithm to generate the optimized fluence map of the beam. More descriptions regarding the generation of an optimized fluence map may be found elsewhere in the present disclosure. See, FIG. 5 and relevant operations thereof. In some embodiments, the optimized fluence map of a beam may be previously generated and stored in a storage device (e.g., the storage device 150 or an external storage device). The processing device 140A may obtain the optimized fluence map of the beam from the storage device and designate the obtained optimized fluence map as the input 710 or part of the input 710.

In some embodiments, the input 70 may be directly inputted into the fluence map generation model 720. Alternatively, the input 710 may be preprocessed (e.g., resampled) and the preprocessed input may be inputted into the fluence map generation model 720.

The output 730 of the fluence map generation model 720 may include composite fluence map(s) I1, I2, . . . , and IN each of which corresponds to one of the N beam(s). The output 730 may be similar to the output 630 as described in connection with FIG. 6, and the descriptions thereof are not repeated here.

In some embodiments, N may be greater than 1, and a plurality of beams may be planned to be delivered to the subject during the treatment. The input 710 of the fluence map generation model 720 may include an input corresponding to each of the beams. For example, the input of the $i^{th}$ beam may include the optimized fluence map Fi. The input of the $i^{th}$ beam may be inputted into the fluence map generation model 720, and the fluence map generation model 720 may output the composite fluence map Ii corresponding to the $i^{th}$ beam. Alternatively, the plurality of beams may share the same input 710, which may include the optimized fluence map of each of the beams. The optimized fluence maps of the beams may be inputted into the fluence map generation model 720 simultaneously, and the fluence map generation model 720 may output the composite fluence maps of the beams jointly.

Figure 8:
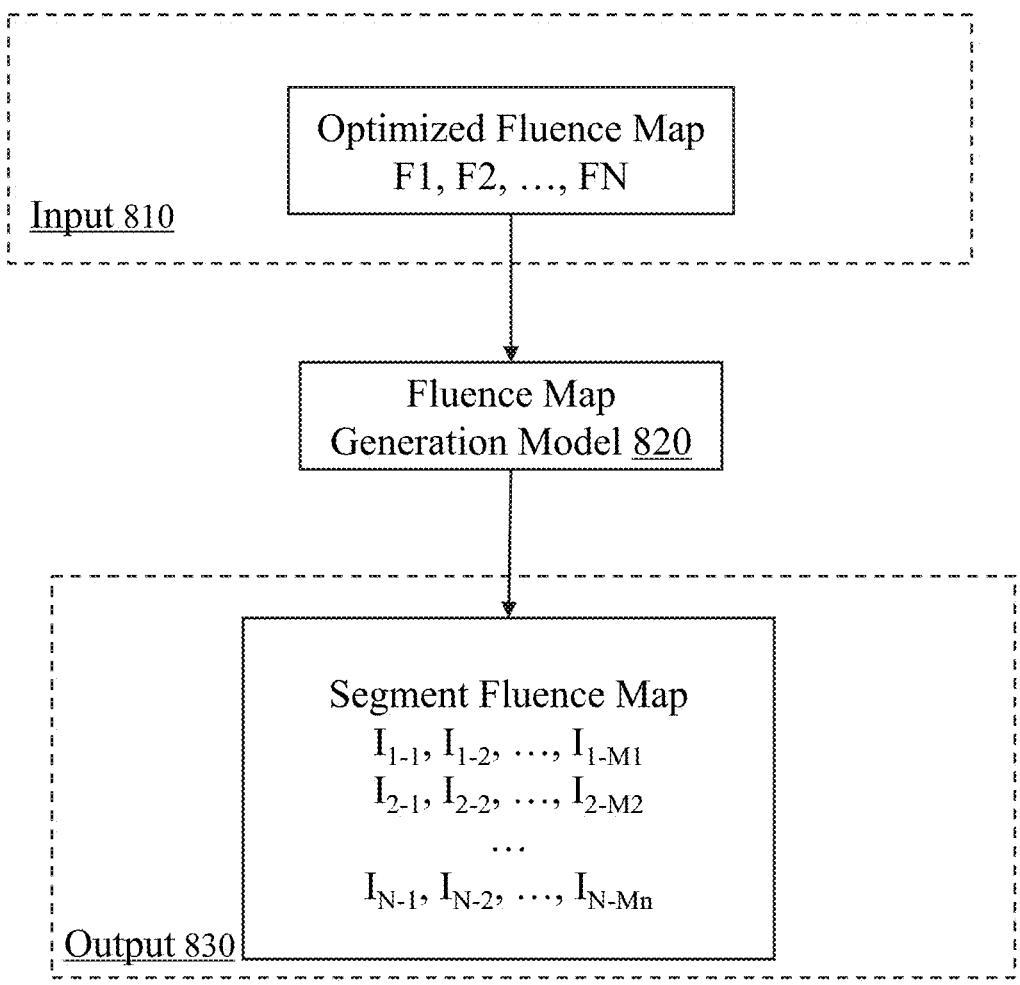
FIG. 8 is a schematic diagram illustrating an exemplary fluence map generation model according to some embodiments of the present disclosure.

FIG. 8 is a schematic diagram illustrating an exemplary fluence map generation model 820 according to some embodiments of the present disclosure.

As shown in FIG. 8, an input 810 of the fluence map generation model 820 may be similar to the input 710 of the fluence map generation model 720 as described in connection with FIG. 7. The input 810 may include the optimized fluence map(s) F1, F2, . . . , and FN of the N beam(s).

An output 830 of the fluence map generation model 820 may include a plurality of segment fluence maps of each of the beam(s). The plurality of segment fluence maps of a beam may correspond to a plurality of segments of the beam. For example, the beam may have Mi segments, wherein Mi may be any positive integer greater than 1. The counts of segments of different beams may be the same or different. As illustrated in FIG. 8, the output 830 of the fluence map generation model 820 may include segment fluence maps $I_{i\text{-}1}, I_{i\text{-}2}, \ldots, I_{i\text{-}Mi}$ corresponding to the $i^{th}$ beam. Each of the segment fluence maps $I_{i\text{-}1}, I_{i\text{-}2}, \ldots, I_{i\text{-}Mi}$ may correspond to one of the Mi segments of the $i^{th}$ beam.

In some embodiments, the optimized fluence map of each of the beams may be inputted into the fluence map generation model 820 separately, and the fluence map generation model 820 may output the segment fluence maps of different beams separately. Alternatively, the optimized fluence maps of the beams may be inputted into the fluence map generation model 820 simultaneously, and the fluence map generation model 820 may output the segment fluence maps of different beams jointly.

As described elsewhere in this disclosure (e.g., FIG. 5 and the relevant descriptions), a conventional treatment planning technique may need to generate a preliminary fluence map of a beam, optimize the preliminary fluence map to generate an optimized fluence map of the beam, and further divide the optimized fluence map of the beam into at least one deliverable fluence map of the beam. The division of the optimized fluence map of the beam may often involve an iterative or manual optimization process of a plurality of preliminary segment fluence maps. Compared with the conventional treatment planning technique, the systems and methods that utilize the fluence map generation model 720 or 820 disclosed herein may obviate the need of iteratively or manually updating the preliminary segment fluence maps, which may improve the efficiency of treatment planning by, e.g., reducing the workload of a user, cross-user variations, and/or the time needed for the treatment planning.

As described in connection with FIG. 7, the fluence map generation model 720 may output a composite fluence map of a beam, and the composite fluence map may need to be converted into a plurality of segment fluence maps of a plurality of segments of the beam. Compared with the fluence map generation model 720, the fluence map generation model 820 may directly output the segment fluence maps of a beam, which may obviate the need of converting the composite fluence map of the beam and improve the efficiency of the treatment planning. In some embodiments, as described in connection with FIG. 6, a plurality of fluence map generation models 620 corresponding to different human parts may be trained and a specific fluence map generation model 620 may be selected according to the target of the subject. Compared with the fluence map generation models 620, the fluence map generation model 720 and/or the fluence map generation model 820 may have a higher universality and be suitable for different human parts.

It should be noted that the above examples illustrated in FIGS. 6 to 8 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, an input of a fluence map generation model may include additional information, such as a dose constrain, a prescription of the subject prescribed by a user (e.g., a doctor, a radiologist). Additionally or alternatively, a portion of an input as described above may be omitted. Merely by way of example, the reference image of the input 610 of the fluence map generation model 620 may be omitted. In some embodiments, an output of a fluence map generation model may include additional information or be without specific information as described above. For example, the output 630 of the fluence map generation model 620 and/or the output 730 of the fluence map generation model 720 may include a plurality of segment fluence maps of each beam. As another example, the output 830 may include a composite fluence map of each beam.

FIG. 9 is a flowchart illustrating an exemplary process for generating a fluence map generation model according to some embodiments of the present disclosure. In some embodiments, process 900 may be executed by the RT planning system 100. For example, the process 900 may be implemented as a set of instructions (e.g., an application)

stored in a storage device (e.g., the storage device 150, the storage device 220, and/or the storage 390). In some embodiments, the processing device 140B (e.g., the processor 210 of the computing device 200, the CPU 340 of the mobile device 300, and/or one or more modules illustrated in FIG. 4B) may execute the set of instructions and accordingly be directed to perform the process 900. In some embodiments, one or more operations of the process 900 may be performed to achieve at least part of operation 520 as described in connection with FIG. 5. In some embodiments, the process 900 may be performed by another device or system other than the RT planning system 100, e.g., a device or system of a vendor of a manufacturer. For illustration purposes, the implementation of the process 900 by the processing device 140B is described as an example.

In 910, the processing device 140B (e.g., the acquisition module 403) may obtain at least one training sample.

In some embodiments, a training sample may include sample planning information and at least one ground truth deliverable fluence map. The sample planning information of the training sample may relate to at least one sample beam to be delivered to a sample subject. The sample subject may be of the same type as or a different type from the subject as described in connection with 510. For example, the subject may be the head of a patient, and the sample subject may be the head (or another portion) of another patient or a man-made subject (e.g., a phantom). The sample planning information of the sample subject refers to planning information of the sample subject. For example, the sample planning information may include sample feature information of the sample subject, sample feature information (e.g., sample segmentation information) of one or more sample ROIs of the sample subject, a sample beam angle of each of the at least one sample beam, a sample reference image of the sample subject, a sample optimized fluence map of each of the at least one beam, a dose constrain, a prescription of the sample subject prescribed by a user (e.g., a doctor, a radiologist), or the like, or any combination thereof. The sample segmentation information of a sample ROI refers to segmentation information of the sample ROI. The sample beam angle of a sample beam refers to a beam angle of the sample beam. The sample reference image of the sample subject refers to a reference image (e.g., a planning image) of the sample subject.

The at least one ground truth deliverable fluence map of the training sample may relate to at least one sample segment of each of the at least one sample beam. For example, the sample beam of a training sample may include a plurality of sample segments, and the at least one ground truth deliverable fluence map relating to a plurality of sample segments of a sample beam may include a ground truth composite fluence map of the sample segments, a ground truth segment fluence map of each of the sample segments, or the like, or any combination thereof. As another example, the sample beam of a training sample may include only one sample segment, and the at least one ground truth deliverable fluence map of the training sample may include a ground truth segment fluence map of the sample segment. For illustration purposes, the following descriptions are described with reference to a training sample, the sample beam of which has a plurality of sample segments, and not intended to limit the scope of the present disclosure.

In some embodiments, a training sample (or a portion thereof) may be previously generated by a computing device (e.g., the processing device 140B) and stored in a storage device (e.g., the storage device 150, the storage device 220, the storage 390, or an external database). The processing device 140B may retrieve the training sample (or a portion thereof) from the storage device. Alternatively, the training sample (or a portion thereof) may be generated by the processing device 140B. Merely by way of example, the processing device 140B may perform one or more operations of process 1000 as described in connection with FIG. 10 to generate at least one ground truth deliverable fluence map of a training sample.

In some embodiments, a first fluence map generation model, which may be same as or similar to the fluence map generation model 620, may be generated by performing the process 900. In such cases, the sample planning information of a training sample may include a sample reference image of a sample subject, sample segmentation information of one or more sample ROIs (e.g., a target or an OAR) of the sample subject, a sample beam angle of each sample beam to be delivered to the sample subject, or the like, or any combination thereof. The at least one ground truth deliverable fluence map of the training sample may include a ground truth composite fluence map of each sample beam.

In some embodiments, a second fluence map generation model, which may be same as or similar to the fluence map generation model 720, may be generated by performing the process 900. In such cases, the sample planning information of a training sample may include a sample optimized fluence map of each sample beam to be delivered to a sample subject. The at least one ground truth deliverable fluence map of the training sample may include a ground truth composite fluence map of each sample beam.

In some embodiments, a third fluence map generation model, which may be same as or similar to the fluence map generation model 820, may be generated by performing the process 900. In such cases, the sample planning information of a training sample may include a sample optimized fluence map of each sample beam to be delivered to a sample subject. The at least one ground truth deliverable fluence map of the training sample may include a plurality of ground truth segment fluence maps of each sample beam.

In some embodiments, for different training samples of the fluence map generation model (e.g., the first, second, third fluence map generation model), the targets of the corresponding sample subjects may be the same or substantially the same. For example, for the first fluence map generation model, the targets of sample subjects of different training samples may be the same or substantially the same. Merely by way of example, a plurality of training samples of a plurality of sample patients who have lung cancer may be used to generate a first fluence map generation model corresponding to human lungs. The first fluence map generation model corresponding to human lungs may be used in treatment planning for a patient who has lung cancer. As yet another example, for the second or the third fluence map generation model, the targets of sample subjects of different training samples may be the same or different.

In 920, the processing device 140B (e.g., the training module 404) may generate the fluence map generation model by training a preliminary model using the at least one training sample.

In some embodiments, the preliminary model may be of any type of model (e.g., a machine learning model), for example, a neural network model (e.g., a CNN model, a GAN model), or the like. The preliminary model may include one or more model parameters. For example, the preliminary model may be a CNN model and exemplary model parameters of the preliminary model may include the number (or count) of layers, the number (or count) of kernels, a kernel size, a stride, a padding of each convolutional layer, a loss function, or the like, or any combination thereof. Before training, the model parameter(s) of the preliminary model may have their respective initial values. For example, the processing device 140B may initialize parameter value(s) of the model parameter(s) of the preliminary model.

In some embodiments, the preliminary model may be trained according to a machine learning algorithm as described elsewhere in this disclosure (e.g., FIG. 5 and the relevant descriptions). For example, the processing device 140B may generate the fluence map generation model according to a supervised machine learning algorithm by performing one or more iterations to iteratively update the model parameter(s) of the preliminary model. For illustration purposes, an exemplary current iteration of the iteration(s) is described in the following description. The current iteration may be performed based on at least a portion of a plurality of training samples. In some embodiments, a same set or different sets of training samples may be used in different iterations in training the preliminary model.

In the current iteration, for each of at least a portion of the training samples, the processing device 140B may generate or obtain a sample input based on the sample planning information of the training sample. The generation of a sample input of a training sample may be performed in a similar manner as the generation of the input of the fluence map generation model as described in connection with operation 520, and the descriptions thereof are not repeated here. For each of the at least a portion of the training samples, the processing device 140B may generate at least one predicted deliverable fluence map by inputting the sample input of the training sample into an updated preliminary model determined in a previous iteration. The processing device 140B may then determine a value of a loss function of the updated preliminary model based on the at least one predicted deliverable fluence map and the at least one ground truth deliverable fluence map of each of the at least a portion of the training samples. The loss function may be used to evaluate the accuracy and reliability of the updated preliminary model, for example, the smaller the loss function is, the more reliable the updated preliminary model is. Exemplary loss functions may include an L1 loss function, a focal loss function, a log loss function, a cross-entropy loss function, a Dice loss function, etc. The processing device 1406 may further update the value(s) of the model parameter(s) of the updated preliminary model to be used in a next iteration based on the value of the loss function according to, for example, a backpropagation algorithm.

In some embodiments, the one or more iterations may be terminated if a termination condition is satisfied in the current iteration. An exemplary termination condition may be that the value of the loss function obtained in the current iteration is less than a predetermined threshold. Other exemplary termination conditions may include that a certain count of iterations is performed, that the loss function converges such that the differences of the values of the loss function obtained in consecutive iterations are within a threshold, etc. If the termination condition is satisfied in the current iteration, the processing device 1406 may designate the updated preliminary model as the fluence map generation model.

It should be noted that the above description regarding the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 900 may be accomplished with one or more additional operations not described and/or without one or more of the operations discussed above. For example, after the fluence map generation model is generated, the processing device 1406 may further test the fluence map generation model using a set of testing samples. Additionally or alternatively, the processing device 140B may update the fluence map generation model periodically or irregularly based on one or more newly-generated training samples (e.g., new treatment plans generated in medical treatment). As yet another example, a training sample (or a portion thereof) may be preprocessed before the training of the preliminary model. Merely by way of example, one or more image processing operations (e.g., image cropping, image resampling) may be performed on a sample reference image and/or a sample optimized fluence map of a training sample.

Figure 10:
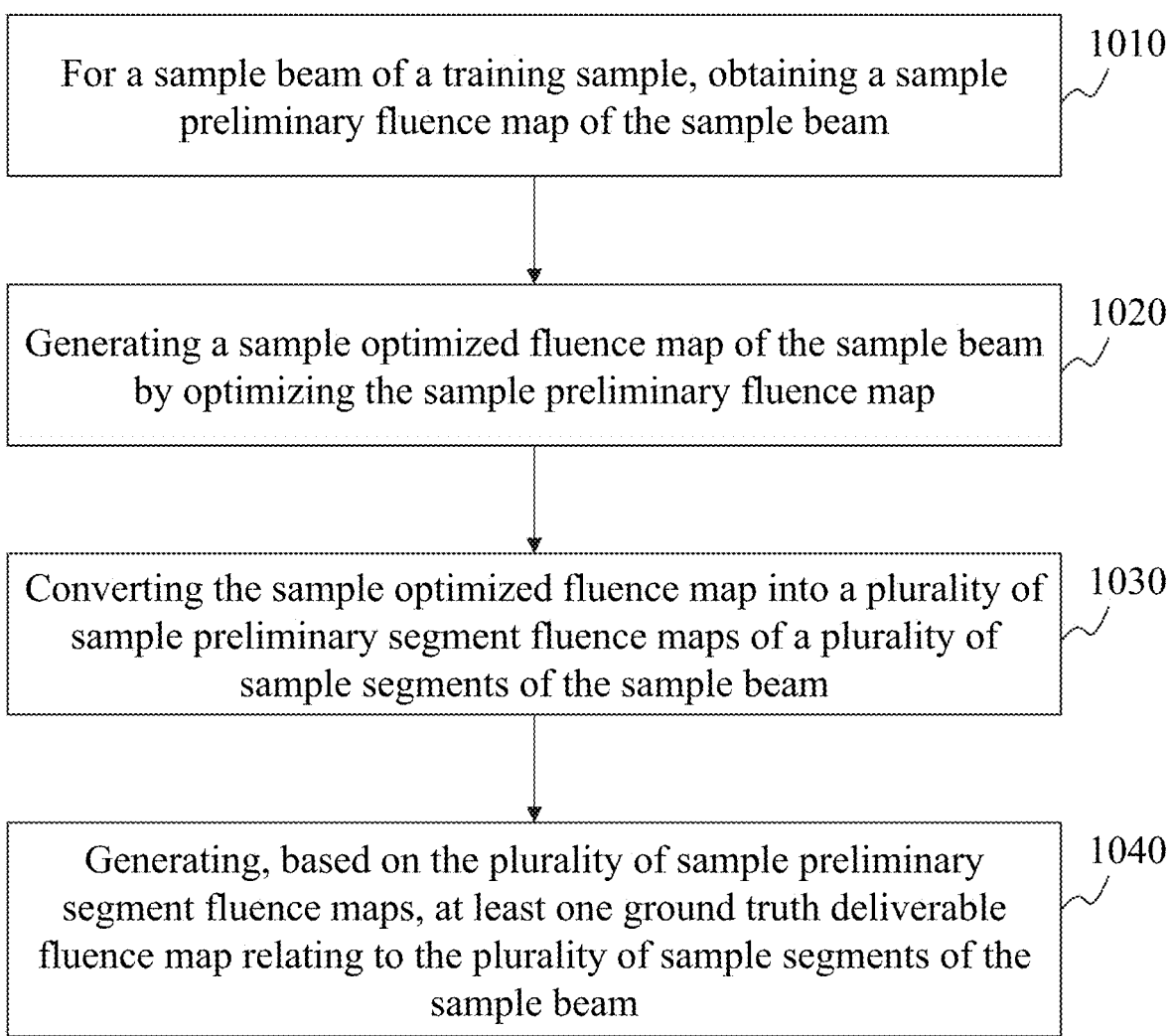
FIG. 10 is a flowchart illustrating an exemplary process for generating at least one ground truth deliverable fluence map of a training sample according to some embodiments of the present disclosure.

FIG. 10 is a flowchart illustrating an exemplary process for generating at least one ground truth deliverable fluence map of a training sample according to some embodiments of the present disclosure. In some embodiments, process 1000 may be executed by the RT planning system 100. For example, the process 1000 may be implemented as a set of instructions (e.g., an application) stored in a storage device (e.g., the storage device 150, the storage device 220, and/or the storage 390). In some embodiments, the processing device 140B (e.g., the processor 210 of the computing device 200, the CPU 340 of the mobile device 300, and/or one or more modules illustrated in FIG. 4B) may execute the set of instructions and accordingly be directed to perform the process 1000. In some embodiments, one or more operations of the process 1000 may be performed to achieve at least part of operation 910 as described in connection with FIG. 9.

As described in connection with operation 910, a training sample may include sample planning information relating to one or more sample beams to be delivered to a sample subject and at least one ground truth deliverable fluence map relating to a plurality of sample segments of each sample beam. The at least one ground truth deliverable fluence map of a sample beam may include a ground truth composite fluence map of the sample segments of the sample beam, a ground truth segment fluence map of each sample segment of the sample beam, or the like. In some embodiments, the processing device 140B may implement the process 1000 for each sample beam of a training sample to generate the at least one deliverable fluence map of the sample beam. For illustration purposes, the implementation of the process 1000 for one sample beam is described as an example.

In 1010, for a sample beam to be delivered to a sample subject, the processing device 140B (e.g., the generation module 405) may obtain a sample preliminary fluence map of the sample beam.

In some embodiments, the sample preliminary fluence map may be generated based on a planning image of the sample subject. The sample preliminary fluence map of the sample beam may be similar to the preliminary fluence map of a beam as described in connection with FIG. 5.

In 1020, the processing device 140B (e.g., the generation module 405) may generate a sample optimized fluence map of the sample beam by optimizing the sample preliminary fluence map. For example, the optimization of the sample preliminary fluence map may be performed based on one or more fluence map optimization algorithms as described elsewhere in this disclosure (e.g., FIG. 5 and the relevant descriptions).

In 1030, the processing device 140B (e.g., the generation module 405) may convert the sample optimized fluence map into a plurality of sample preliminary segment fluence maps of a plurality of sample segments of the sample beam. Each of the sample preliminary segment fluence maps may correspond to one of the sample segments of the sample beam. For example, the sample optimized fluence map may be converted into the sample preliminary segment fluence maps according to a leaf sequencing algorithm.

In 1040, the processing device 140B (e.g., the generation module 405) may generate, based on the plurality of sample preliminary segment fluence maps, the at least one ground truth deliverable fluence map relating to the plurality of sample segments.

In some embodiments, an error may exist between the sample optimized fluence map and a composite fluence map of the sample preliminary segment fluence maps. The sample preliminary segment fluence maps may need to be optimized to generate a plurality of sample optimized segment fluence maps, which make a composite fluence map of the sample optimized segment fluence maps matches the sample optimized fluence map. As used herein, two fluence maps may be regarded as matching each other if a degree of similarity between the two fluence maps exceeds a threshold similarity.

In some embodiments, the optimization of the sample preliminary segment fluence maps may be performed automatically, semi-automatically, or manually. For example, the processing device 140B may iteratively update the sample preliminary segment fluence maps according to one or more fluence map optimization algorithms. As another example, a user (e.g., a doctor, a radiologist) may manually adjust parameter(s) of the sample segments and/or the sample preliminary segment fluence maps via, e.g., an interface implemented on a terminal device. As yet another example, the processing device 140B may iteratively update the sample preliminary segment fluence maps according to one or more fluence map optimization algorithms in combination with user intervention (e.g., an adjustment to or a confirmation of a preliminary optimization result generated by the processing device 140B).

After the preliminary segment fluence maps are optimized, the processing device 1406 may designate the sample optimized segment fluence maps as the ground truth segment fluence maps of the sample segments. Additionally or alternatively, the processing device 1406 may designate a composite fluence map of the sample optimized segment fluence maps as a ground truth composite fluence map of the sample segments.

It should be noted that the above description regarding the process 1000 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1000 may be accomplished with one or more additional operations not described and/or without one or more of the operations discussed above. For example, operations 1010 and 1020 may be integrated into a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for radiotherapy planning, comprising:
at least one storage device including a set of instructions; and
at least one processor configured to communicate with the at least one storage device, wherein when executing the set of instructions, the at least one processor is configured to perform operations including:
obtaining planning information relating to at least one beam to be delivered to a subject in a treatment of the subject;
generating, based on the planning information, an input of a fluence map generation model; and
for each of the at least one beam, generating, based on the input of the fluence map generation model, at least one deliverable fluence map relating to a plurality of segments of each of the at least one beam.

2. The system of claim 1, wherein the planning information comprises:
segmentation information of one or more regions of interest (ROIs) of the subject to which the at least one beam is to be delivered; and
a beam angle of each of the at least one beam.

3. The system of claim 2, wherein the planning information further comprises a reference image of the subject.

4. The system of claim 1, wherein the planning information comprises an optimized fluence map of each of the at least one beam.

5. The system of claim 4, wherein the obtaining planning information relating to at least one beam to be delivered to a subject in a treatment of the subject comprises:
for each of the at least one beam,
obtaining a preliminary fluence map of each of the at least one beam; and
generating the optimized fluence map of each of the at least one beam by optimizing the preliminary fluence map.

6. The system of claim 1, wherein the at least one processor is further configured to generate the fluence map generation model according to a training process including:
obtaining at least one training sample, each of which includes sample planning information and at least one ground truth deliverable fluence map, the sample planning information relating to at least one sample beam to be delivered to a sample subject, and the at least one ground truth deliverable fluence map relating to at least one sample segment of each of the at least one sample beam; and
generating the fluence map generation model by training a preliminary model using the at least one training sample.

7. The system of claim 6, wherein the at least one processor is further configured to obtain each of the at least one training sample by:
for each of the at least one sample beam corresponding to each of the at least one training sample,
obtaining a sample preliminary fluence map of each of the at least one sample beam;

generating a sample optimized fluence map of each of the at least one sample beam by optimizing the sample preliminary fluence map;

converting the sample optimized fluence map into at least one sample preliminary segment fluence map of the at least one sample segment of each of the at least one sample beam; and generating, based on the at least one sample preliminary segment fluence map, the at least one ground truth deliverable fluence map relating to the at least one sample segment of each of the at least one sample beam.

8. The system of claim 1, wherein the fluence map generation model includes at least one of a convolutional neural network (CNN) or a generative adversarial network (GAN).

9. The system of claim 1, wherein the at least one deliverable fluence map comprises at least one of:

a composite fluence map of the plurality of segments; or a plurality of segment fluence maps, each of which corresponds to one of the plurality of segments.

10. A method implemented on a computing device having at least one processor and at least one computer-readable storage medium for radiotherapy planning, the method comprising:

obtaining planning information relating to at least one beam to be delivered to a subject in a treatment of the subject;

generating, based on the planning information, an input of a fluence map generation model; and for each of the at least one beam, generating, based on the input of the fluence map generation model, at least one deliverable fluence map relating to a plurality of segments of each of the at least one beam.

11. The method of claim 10, wherein the planning information comprises:

segmentation information of one or more regions of interest (ROIs) of the subject to which the at least one beam is to be delivered; and a beam angle of each of the at least one beam.

12. The method of claim 11, wherein the planning information further comprises a reference image of the subject.

13. The method of claim 10, wherein the planning information comprises an optimized fluence map of each of the at least one beam.

14. The method of claim 13, wherein the obtaining planning information relating to at least one beam to be delivered to a subject in a treatment of the subject comprises:

for each of the at least one beam, obtaining a preliminary fluence map of each of the at least one beam; and generating the optimized fluence map of each of the at least one beam by optimizing the preliminary fluence map.

15. The method of claim 10, wherein the fluence map generation model is generated according to a training process including:

obtaining at least one training sample, each of which includes sample planning information and at least one ground truth deliverable fluence map, the sample planning information relating to at least one sample beam to be delivered to a sample subject, and the at least one ground truth deliverable fluence map relating to at least one sample segment of each of the at least one sample beam; and generating the fluence map generation model by training a preliminary model using the at least one training sample.

16. The method of claim 15, wherein each of the at least one training sample is obtained by:

for each of the at least one sample beam corresponding to each of the at least one training sample, obtaining a sample preliminary fluence map of each of the at least one sample beam;

generating a sample optimized fluence map of each of the at least one sample beam by optimizing the sample preliminary fluence map;

converting the sample optimized fluence map into at least one sample preliminary segment fluence map of the at least one sample segment of each of the at least one sample beam; and generating, based on the at least one sample preliminary segment fluence map, the at least one ground truth deliverable fluence map relating to the at least one sample segment of each of the at least one sample beam.

17. The method of claim 10, wherein the fluence map generation model includes at least one of a convolutional neural network (CNN) or a generative adversarial network (GAN).

18. The method of claim 10, wherein the at least one deliverable fluence map comprises at least one of:

a composite fluence map of the plurality of segments; or a plurality of segment fluence maps, each of which corresponds to one of the plurality of segments.

19. A non-transitory computer readable medium, comprising a set of instructions for radiotherapy planning, wherein when executed by at least one processor, the set of instructions direct the at least one processor to effectuate a method, the method comprising:

obtaining planning information relating to at least one beam to be delivered to a subject in a treatment of the subject;

generating, based on the planning information, an input of a fluence map generation model; and for each of the at least one beam, generating, based on the input of the fluence map generation model, at least one deliverable fluence map relating to a plurality of segments of each of the at least one beam.

20. The non-transitory computer readable medium of claim 19, wherein the at least one deliverable fluence map comprises at least one of:

a composite fluence map of the plurality of segments; or a plurality of segment fluence maps, each of which corresponds to one of the plurality of segments.

* * * * *